US010004236B2

(12) United States Patent
Glare et al.

(10) Patent No.: US 10,004,236 B2
(45) Date of Patent: Jun. 26, 2018

(54) BIOCONTROL COMPOSITIONS

(71) Applicants: Travis Robert Glare, Linclon (NZ); John Graham Hampton, Christchurch (NZ); Murray Paul Cox, Palmerston North (NZ); Damian Alexander Bienkowski, Christchurch (NZ)

(72) Inventors: Travis Robert Glare, Linclon (NZ); John Graham Hampton, Christchurch (NZ); Murray Paul Cox, Palmerston North (NZ); Damian Alexander Bienkowski, Christchurch (NZ)

(73) Assignee: Lincoln University, Canterbury (NZ)

( * ) Notice: Subject to any disclaimer, the term of this patent is extended or adjusted under 35 U.S.C. 154(b) by 1108 days.

(21) Appl. No.: 13/837,735

(22) Filed: Mar. 15, 2013

(65) Prior Publication Data

US 2014/0086876 A1  Mar. 27, 2014

Related U.S. Application Data

(60) Provisional application No. 61/704,801, filed on Sep. 24, 2012.

(51) Int. Cl.
| A01N 63/00 | (2006.01) |
| C12N 1/20 | (2006.01) |
| C12R 1/01 | (2006.01) |
| A01P 7/04 | (2006.01) |

(52) U.S. Cl.
CPC ............... *A01N 63/00* (2013.01); *C12R 1/01* (2013.01)

(58) Field of Classification Search
None
See application file for complete search history.

(56) References Cited

U.S. PATENT DOCUMENTS

| 5,045,314 A | 9/1991 | Bone et al. |
| 5,055,293 A | 10/1991 | Aronson et al. |
| 6,706,860 B2 | 3/2004 | Boets et al. |
| 7,919,609 B2 | 4/2011 | Boets et al. |
| 2002/0120114 A1 | 8/2002 | Schnepf et al. |

(Continued)

FOREIGN PATENT DOCUMENTS

| EP | 2 079 314 B1 | 3/2010 |
| WO | WO 2013/050867 A2 | 4/2013 |

OTHER PUBLICATIONS

Lester et al. "Container surface area and water depth influence the population dynamics of the mosquito *Culex pervigilans* (*Diptera*: Culcidae) and its associated predators in New Zealand." Journal of Vector Ecology, Dec. 2003.*

(Continued)

*Primary Examiner* — Blaine Lankford
*Assistant Examiner* — Lauren K Van Buren
(74) *Attorney, Agent, or Firm* — Leydig, Voit & Mayer, Ltd.

(57) ABSTRACT

The invention provides isolated *Brevibacillius laterosporus* strains with insecticidal activity against at least one *Lepidoptera* species and at least one *Diptera* species. In particular the invention provides the isolated *B. laterosporus* strains NMI No. V12/001946, NMI No. V12/001945 and NMI No. V12/001944. The invention provides compositions comprising one or more strain of the invention. The invention also provides methods of use of one or more strains or compositions of the inventions to control pests, particularly insect pests.

13 Claims, 13 Drawing Sheets

(56) References Cited

U.S. PATENT DOCUMENTS

2008/0214443 A1* 9/2008 Baum .............. C12N 15/8286
514/1.1
2010/0003227 A1* 1/2010 Floris .................. A01N 63/00
424/93.46

OTHER PUBLICATIONS

Baxter et al. (Oct. 2011) "Parallel evolution of Bacillus thuringiensis toxin resistance in Lepidoptera," Genetics. 189:675-679.
de Maagd et al. (2003) "Structure, diversity and evolution of protein toxins from spore-forming entomopathogenic bacteria," Annual Review of Genetics. 37:409-433.
de Oliveira et al. (2004) "Molecular characterization of *Brevibacillus laterosporus* and its potential use in biological control," Appl. Environ. Microbiol. 70(11):6657-6664.
Erturk et al. (2006) "Studies on bacterial flora and biological control agent of *Cydia pomonella* L. (*Lepidoptera*: Tortricididae)," African Journal of Biotechnology.5(22):2081-2085.
Favret et al. (1985) "Insecticidal activity of Bacillus laterosporus," J. Invertebrate Pathology. 48:195-203.
Huang et al. (2005) "An extracellular protease from Brevibacillus laterosporus G4 without parasporal crystals can serve as a pathogenic factor in infection of nematodes," Res. Microbiol. 156(5-6):719-727.
Orlova et al. (1998) "Insecticidal activity of Bacillus laterosporus," Appl. Environ. Microbiol. 64(7):2723-2725.
Prasanna et al. (Apr. 29, 2012) "A novel strain of Brevibacillus laterosporus produces chitinases that contribute to its biocontrol potential," Applied Microbiology and Biotechnology. 97:1601-1611.

Rivers et al. (1991) "Mosquitocidal activity Bacillus laterosporus," Journal of Invertebrate Pathology. 58:444-447.
Ruiu et al. (2006) "Lethal and sublethal effects of Brevibacillus laterosporus on the housefly (*Musca domestica*)," Entomologia Experimentalis et Applicata. 118(2):137-144.
Shida et al. (1996) "Proposal for two new genera, *Brevibacillus* gen. nov. and *Aneurinibacillus* gen. nov.," Int. J. Syst. Bacteriol. 46(4):939-946.
Singer (1996) "The utility of strains of morphological group II Bacillus," Advances in Applied Microbiology. 42:219-261.
Singer et al. (1997) "Biological control of the zebra mussel *Dreissena polymorpha* and the snail *Biomphalaria glabrata*, using Gramicidin S and D and molluscicidal strains of Bacillus," J. Ind. Microbiol. Biotechnol. 18(4):226-231.
Singh (1983) "A general purpose laboratory diet mixture for rearing insects," Insect Sci. Application. 4:357-362.
Tabashnik et al. (1990) "Field Development of Resistance to *Bacillus thuringiensis* in Diamondback Moth (Lepidoptera: Plutellidae)," Journal of Economic Entomology. 83:1671-1676.
Tabashnik et al. (1998) "Insect resistance to *Bacillus thuringiensis*: uniform or diverse?" Phil. Trans. R. Soc. Lond. B. 353:1751-1756.
Wearing et al. (2003) "Screening for resistance in apple cultivars to lightbrown apple moth, *Epiphyas postvittana*, and greenheaded leafroller, *Planotortrix octo*, and its relationship to field damage," Entomologia Experimentalis et Applicata. 109:39-53.
Zahner et al. (1999) "Genotypic diversity among Brevibacillus laterosporus strains," Applied and Environmental Microbiology. 65(11):5182-5185.
International Preliminary Report on Patentability with Claim Amendments corresponding to International Patent Application No. PCT/IB2013/055157,completed Sep. 17, 2014.
International Search Report with Written Opinion corresponding to International Patent Application No. PCT/IB2013/055157, dated Nov. 15, 2013.

* cited by examiner

| | | |
|---|---|---|
| V12/001946 | ACGCTGGCGGCGTGCCTAATACATGCAAGTCGAGCGAGGG | 40 |
| V12/001944 | ---------------------------------------- | 40 |
| V12/001945 | ---------------------------------------- | 40 |
| NCIMB41419 | ---------------------------------------- | 40 |
| | | |
| V12/001946 | TCTTCGGACCCTAGCGGCGGACGGGTGAGTAACACGTAGG | 80 |
| V12/001944 | ---------------------------------------- | 80 |
| V12/001945 | ---------------------------------------- | 80 |
| NCIMB41419 | -T-------------------------------------- | 80 |
| | | |
| V12/001946 | CAACCTGCCTGTAAGACTGGGATAACATAGGGAAACTTAT | 120 |
| V12/001944 | ---------------------------------------- | 120 |
| V12/001945 | ---------------------------------------- | 120 |
| NCIMB41419 | ---------------------------------------- | 120 |
| | | |
| V12/001946 | GCTAATACCGGATAGGGTTTTGCTTCTCCTGAAGCGAAAC | 160 |
| V12/001944 | ---------------------------------------- | 160 |
| V12/001945 | -----------------------------G---------- | 160 |
| NCIMB41419 | --------------A--------------G-A-------- | 160 |
| | | |
| V12/001946 | GGAAAGATGGCGCAAGCTATCACTTACAGATGGGCCTGCG | 200 |
| V12/001944 | ------------------------G--------------- | 200 |
| V12/001945 | ---------------------------------------- | 200 |
| NCIMB41419 | ------------------------G--------------- | 200 |
| | | |
| V12/001946 | GCGCATTAGCTAGTTGGTGAGGTAATGGCTCACCAAGGCG | 240 |
| V12/001944 | ---------------------------------------- | 240 |
| V12/001945 | ---------------------------------------- | 240 |
| NCIMB41419 | --------------------A------------------- | 240 |
| | | |
| V12/001946 | ACGATGCGTAGCCGACCTGAGAGGGTGACCGGCCACACTG | 280 |
| V12/001944 | ---------------------------------------- | 280 |
| V12/001945 | ---------------------------------------- | 280 |
| NCIMB41419 | ---------------------------------------- | 280 |
| | | |
| V12/001946 | GGACTGAGACACGGCCCAGACTCCTACGGGAGGCAGCAGT | 320 |
| V12/001944 | ---------------------------------------- | 320 |
| V12/001945 | ---------------------------------------- | 320 |
| NCIMB41419 | ---------------------------------------- | 320 |
| | | |
| V12/001946 | AGGGAATTTTCCACAATGGACGAAAGTCTGATGGAGCAAC | 360 |
| V12/001944 | ---------------------------------------- | 360 |
| V12/001945 | ---------------------------------------- | 360 |
| NCIMB41419 | ---------------------------------------- | 360 |
| | | |
| V12/001946 | GCCGCGTGAACGATGAAGGCTTTCGGGTCGTAAAGTTCTG | 400 |
| V12/001944 | ---------------------------------------- | 400 |
| V12/001945 | ---------------------------------------- | 400 |
| NCIMB41419 | ---------------------------------------- | 400 |

Figure 10

| | | |
|---|---|---|
| V12/001946 | TTGTTAGGGAAGAAACAGTGCCATTTAAATAAGGTGGCAC | 440 |
| V12/001944 | ---------------------------------------- | 440 |
| V12/001945 | ---------------------------------------- | 440 |
| NCIMB41419 | ---------------------------------------- | 440 |
| V12/001946 | CTTGACGGTACCTAACGAGAAAGCCACGGCTAACTACGTG | 480 |
| V12/001944 | ---------------------------------------- | 480 |
| V12/001945 | ---------------------------------------- | 480 |
| NCIMB41419 | ---------------------------------------- | 480 |
| V12/001946 | CCAGCAGCCGCGGTAATACGTAGGTGGCAAGCGTTGTCCG | 520 |
| V12/001944 | ---------------------------------------- | 520 |
| V12/001945 | ---------------------------------------- | 520 |
| NCIMB41419 | ---------------------------------------- | 520 |
| V12/001946 | GAATTATTGGGCGTAAAGCGCGCGCAGGTGGCTATGTAAG | 560 |
| V12/001944 | ---------------------------------------- | 560 |
| V12/001945 | ---------------------------------------- | 560 |
| NCIMB41419 | ---------------------------------------- | 560 |
| V12/001946 | TCTGATGTTAAAGCCCGAGGCTCAACCTCGGTTCGCATTG | 600 |
| V12/001944 | ---------------------------------------- | 600 |
| V12/001945 | ---------------------------------------- | 600 |
| NCIMB41419 | ----------------G----------------------- | 600 |
| V12/001946 | GAAACTGTGTAGCTTGAGTGCAGGAGAGGAAAGTGGTATT | 640 |
| V12/001944 | ---------------------------------------- | 640 |
| V12/001945 | ---------------------------------------- | 640 |
| NCIMB41419 | -------C-------------------------------- | 640 |
| V12/001946 | CCACGTGTAGCGGTGAAATGCGTAGAGATGTGGAGGAACA | 680 |
| V12/001944 | ---------------------------------------- | 680 |
| V12/001945 | ---------------------------------------- | 680 |
| NCIMB41419 | ---------------------------------------- | 680 |
| V12/001946 | CCAGTGGCGAAGGCGACTTTCTGGCCTGTAACTGACACTG | 720 |
| V12/001944 | ---------------------------------------- | 720 |
| V12/001945 | ---------------------------------------- | 720 |
| NCIMB41419 | ---------------------------------------- | 720 |
| V12/001946 | AGGCGCGAAAGCGTGGGGAGCAAACAGGATTAGATACCCT | 760 |
| V12/001944 | ---------------------------------------- | 760 |
| V12/001945 | ---------------------------------------- | 760 |
| NCIMB41419 | ---------------------------------------- | 760 |
| V12/001946 | GGTAGTCCACGCCGTAAACGATGAGTGCTAGGTGTTAGGG | 800 |
| V12/001944 | ---------------------------------------- | 800 |
| V12/001945 | ---------------------------------------- | 800 |
| NCIMB41419 | ---------------------------------------- | 800 |

Figure 10 cont.

| | | |
|---|---|---|
| V12/001946 | GTTTCAATACCCTTAGTGCCGCAGCTAACGCAATAAGCAC | 840 |
| V12/001944 | ---------------------------------------- | 840 |
| V12/001945 | ---------------------------------------- | 840 |
| NCIMB41419 | ---------------------------------------- | 840 |
| V12/001946 | TCCGCCTGGGGAGTACGCTCGCAAGAGTGAAACTCAAAGG | 880 |
| V12/001944 | ---------------------------------------- | 880 |
| V12/001945 | ---------------------------------------- | 880 |
| NCIMB41419 | ---------------------------------------- | 880 |
| V12/001946 | AATTGACGGGGGCCCGCACAAGCGGTGGAGCATGTGGTTT | 920 |
| V12/001944 | ---------------------------------------- | 920 |
| V12/001945 | ---------------------------------------- | 920 |
| NCIMB41419 | ---------------------------------------- | 920 |
| V12/001946 | AATTCGAAGCAACGCGAAGAACCTTACCAGGTCTTGACAT | 960 |
| V12/001944 | ---------------------------------------- | 960 |
| V12/001945 | ---------------------------------------- | 960 |
| NCIMB41419 | ---------------------------------------- | 960 |
| V12/001946 | CCCACTGACCGCTCTAGAGATAGAGCTTCCCTTCGGGGCA | 1000 |
| V12/001944 | ---------------------------------------- | 1000 |
| V12/001945 | ---------------------------------------- | 1000 |
| NCIMB41419 | ---------------------------------------- | 1000 |
| V12/001946 | GTGGTGACAGGTGGTGCATGGTTGTCGTCAGCTCGTGTCG | 1040 |
| V12/001944 | ---------------------------------------- | 1040 |
| V12/001945 | ---------------------------------------- | 1040 |
| NCIMB41419 | ---------------------------------------- | 1040 |
| V12/001946 | TGAGATGTTGGGTTAAGTCCCGCAACGAGCGCAACCCTTA | 1080 |
| V12/001944 | ---------------------------------------- | 1080 |
| V12/001945 | ---------------------------------------- | 1080 |
| NCIMB41419 | ---------------------------------------- | 1080 |
| V12/001946 | TCTTTAGTTGCCAGCATTCAGTTGGGCACTCTAGAGAGAC | 1120 |
| V12/001944 | ---------------------------------------- | 1120 |
| V12/001945 | ---------------------------------------- | 1120 |
| NCIMB41419 | ---------------------------------------- | 1120 |
| V12/001946 | TGCCGTCGACAAGACGGAGGAAGGCGGGGATGACGTCAAA | 1160 |
| V12/001944 | ---------------------------------------- | 1160 |
| V12/001945 | ---------------------------------------- | 1160 |
| NCIMB41419 | ---------------------------------------- | 1160 |
| V12/001946 | TCATCATGCCCCTTATGACCTGGGCTACACACGTGCTACA | 1200 |
| V12/001944 | ---------------------------------------- | 1200 |
| V12/001945 | ---------------------------------------- | 1200 |
| NCIMB41419 | ---------------------------------------- | 1200 |

Figure 10 cont.

```
V12/001946   ATGGTTGGTACAACGGGATGCTACTTCGCGAGAAGATGCT   1240
V12/001944   ----------------------------------------   1240
V12/001945   ----------------------------------------   1240
NCIMB41419   ----------------------------------------   1240

V12/001946   AATCTCTTAAAACCAATCTCAGTTCGGATTGTAGGCTGCA   1280
V12/001944   ----------------------------------------   1280
V12/001945   ----------------------------------------   1280
NCIMB41419   ----------------------------------------   1280

V12/001946   ACTCGCCTACATGAAGTCGGAATCGCTAGTAATCGCGGAT   1320
V12/001944   ----------------------------------------   1320
V12/001945   ----------------------------------------   1320
NCIMB41419   ----------------------------------------   1320

V12/001946   CAGCATGCCGCGGTGAATACGTTCCCGGGCCTTGTACACA   1360
V12/001944   ----------------------------------------   1360
V12/001945   ----------------------------------------   1360
NCIMB41419   ----------------------------------------   1360

V12/001946   CCGCCCGTCACACCACGGGAGTTTGCAACACCCGAAGTCG   1400
V12/001944   ----------------------------------------   1400
V12/001945   ----------------------------------------   1400
NCIMB41419   ----------------------------------------   1400

V12/001946   GTGAGGTAACCGCAAGGAGCCAGCCGCCGAAGGTGGGGTA   1440
V12/001944   ----------------------------------------   1440
V12/001945   ----------------------------------------   1440
NCIMB41419   ----------------------------------------   1440

V12/001946   GATAACTGGGGTGAAGTCGTAACAAGGTATCCGTACCGGA   1480
V12/001944   ----------------------------------------   1480
V12/001945   ----------------------------------------   1480
NCIMB41419   ----------------------------------------   1480

V12/001946   AGG    (SEQ ID NO: 1)                      1483
V12/001944   ---    (SEQ ID NO: 2)                      1483
V12/001945   ---    (SEQ ID NO: 3)                      1483
NCIMB41419   ---    (SEQ ID NO: 4)                      1483
```

Figure 10 cont.

BIOCONTROL COMPOSITIONS

CROSS-REFERENCE TO RELATED APPLICATION

This application claims the benefit of U.S. provisional application No. 61/704,801 filed Sep. 24, 2012, the entire disclosure of which is incorporated by reference in its entirety.

TECHNICAL FIELD

This invention relates to novel strains of *Brevibacillius laterosporus* and compositions containing same. Methods for the biological control of insect pests including diamondback moth and mosquito using the novel strains and compositions are also provided

BACKGROUND OF THE INVENTION

Insect pests represent a significant economic cost to modern agriculture. Current systems of agriculture often require one or a few crops or plant types to be grown over a large area. Such an ecologically unbalanced system is susceptible to insect pressure.

Some insect pests are also harmful to animal health including humans. For example, mosquitoes are known to carry a variety of diseases. They therefore act as vectors in the spread of disease.

Traditionally, control of insect pests has been pursued through the use of chemical insecticides and pesticides. However, consumers are becoming increasingly concerned about chemical residues and their effects on animal and plant health, and the environment. Moreover, many insect pests are becoming resistant to pesticides and insecticides.

Biological control represents an alternative means of controlling insect pests which reduces dependence on chemicals. Such "natural" methods enjoy greater public acceptance, and may be more effective and sustainable than chemical control methods.

A wide range of biological control agents including bacteria, yeast and fungi have been investigated for use in controlling insect pests. One widely investigated species of bacteria for insecticidal use is *Bacillus*.

*Bacillus* is a genus containing many diverse bacterial species with properties varying from detrimental to animal and plant health, to useful for insect control.

*Bacillus thuringiensis* (Bt) in particular, is a well known biocontrol agent commercially available in products such as Thuricide® and Dipel®.

In recent years there has been evidence of insect resistance to Bt developing. See for example Tabashnik et al (1990); Baxter et al (2011); and Tabashnik et al (1998).

Accordingly, there is still a need for new *Bacillus* species for use in the control of pests including insect pests.

The applicants have now identified a number of new *Brevibacillius laterosporus* that are effective as biocontrol agents.

One object of the present invention is therefore to provide novel strains of *B. laterosporus* useful as biocontrol agents. Another object is to provide a composition comprising at least one of the novel *B. laterosporus* strains of the invention; and/or to at least provide the public with a useful choice.

SUMMARY OF THE INVENTION

In one aspect the invention provides an isolated *Brevibacillius laterosporus* strain with insecticidal activity against at least one Lepidoptera species and at least one Diptera species.

In one embodiment the at least one Lepidoptera species is diamondback moth (*Plutella xylostella*).

In one embodiment the at least one Lepidoptera species is cabbage looper moth (*Trichoplusia ni*).

In one embodiment the at least one Lepidoptera is selected from a Tortricidae and a Plutellidae.

In a further embodiment the at least one Diptera species is a mosquito species.

In a further embodiment the mosquito species is selected from *Culex pervigilans* and *Opifex fuscus*.

In a further embodiment the *B. laterosporus* strain is active against both diamondback moth (*Plutella xylostella*) and at least one mosquito species selected from *Culex pervigilans* and *Opifex fuscus*.

In one embodiment the *B. laterosporus* strain is in the form of a biologically pure culture.

The isolated *B. laterosporus* strains or biologically pure cultures may be selected from strains NMI No. V12/001946, NMI No. V12/001945 and NMI No. V12/001944.

In one aspect the invention provides biologically pure culture of *Brevibacillius laterosporus* strain NMI No. V12/001946.

In a further aspect the invention provides biologically pure culture of *Brevibacillius laterosporus* strain NMI No. V12/001945.

In a further aspect the invention provides biologically pure culture of *Brevibacillius laterosporus* strain NMI No. V12/001944.

In another aspect, the invention provides a composition comprising at least one *B. laterosporus* strain of the invention, and an agriculturally acceptable carrier.

In one embodiment, the invention provides a composition comprising one or more strains of *B. laterosporus* selected from NMI No. V12/001946, NMI No. V12/001945 and NMI No. V12/001944 and an agriculturally acceptable carrier.

In one embodiment the composition may comprise two *B. laterosporus* strains of the invention. In another embodiment the composition may comprise three *B. laterosporus* strains of the invention.

In one embodiment the composition consists essentially of one or more strains of *B. laterosporus* selected from NMI No. V12/001946, NMI No. V12/001945 and NMI No. V12/001944, and an agriculturally acceptable carrier.

In one embodiment the composition consists essentially of two *B. laterosporus* strains of the invention and an agriculturally acceptable carrier. In another embodiment the composition consists essentially of three *B. laterosporus* strains of the invention.

The composition in one embodiment is an insecticide composition.

In another aspect, the invention provides a method for controlling at least one pest, the method comprising contacting the at least one pest with a composition of the invention.

In another aspect, the invention provides a method for controlling at least one pest, the method comprising contacting the at least one pest with one or more *B. laterosporus* strains of invention.

Preferably, the at least one pest is an insect pest, and more particularly the at least one pest is selected from a Lepidoptera and a Diptera.

Application of the strain, strains or composition of the invention in the method of the invention my control more than one type of pest.

Thus in a further embodiment, the at least one pest is an insect pest, selected from a Lepidoptera, a Diptera or is both.

In one embodiment the at least one insect pest is selected from a diamondback moth and a mosquito.

In a further embodiment, the at least one pest is an insect pest selected from a diamondback moth, a mosquito, or is both.

In one embodiment the Lepidoptera is selected from a Tortricidae, Plutellidae and Noctuidae. In a particular embodiment the Lepidoptera is selected from a Tortricidae and a Plutellidae.

In another embodiment the at least one insect pest is a moth. The moth in one embodiment is selected from the group consisting of a diamondback moth (*Plutella xylostella*), a cabbage looper moth (*Trichoplusia ni*), a codling moth (*Cydia pomonella*), a common forest looper moth (*Pseudocoremia suavis*), cotton bollworm moth (*Helicoverpa armigera*), a light brown apple moth (*Epiphyas postvittana*), a blacklegged leafroller moth (*Planotortrix notophaea*), and a black lyre leafroller (*Cnephasia jactatana*).

In another embodiment the pest is a nematode. In a particular embodiment, the nematode is a microworm. Preferably the microworm is *Panagrellus redivivus*.

In another embodiment the insect pest is a wasp. In a particular embodiment the wasp is *Vespula vulgaris*.

In another embodiment the insect pest is a Manuka beetle (*Pyronta* sp.)

Definitions

The term "insecticide" as used herein refers to agents which act to kill or control the growth of insects.

The term "contacting" as used herein refers to the provision of a composition or strain(s) of the invention to a pest in a manner useful to effect pest control. Most commonly contacting will involve the pest feeding on material comprising a composition or strain(s) of the invention but is not limited thereto. Accordingly, "contacting" includes feeding.

The term "control", "controlling", "biocontrol" or "biological control" are used interchangeably herein to refer to reduction in numbers of pests, particularly insect pests, accomplished using the strains or compositions of the invention. Generally comprehended is the reduction in numbers, or eradication of pests, or inhibition of their rate of reproduction.

The term "comprising" as used in this specification means "consisting at least in part of". When interpreting each statement in this specification that includes the term "comprising", features other than that or those prefaced by the term may also be present. Related terms such as "comprise" and "comprises", and the terms "including", "include" and "includes" are to be interpreted in the same manner.

The term "consisting essentially of" when used in this specification refers to the features stated and allows for the presence of other features that do not materially alter the basic characteristics of the features specified.

The term "agriculturally acceptable carrier" covers all liquid and solid carriers known in the art such as water and oils, as well as adjuvants, dispersants, binders, wettants, surfactants, humectants tackifiers, and the like that are ordinarily known for use in the preparation of control compositions, including insecticide compositions.

The term "effective amount" as used herein means an amount effective to control or eradicate pests, particularly insect pests.

The term "biologically pure culture" or "biologically pure isolate" as used herein refers to a culture of a *B. laterosporus* strain of the invention comprising at least 90%, preferably 95%, preferably 99% and more preferably at least 99.5% cells of the *B. laterosporus* strain.

The term "pest" as used herein refers to organisms that are of inconvenience to humans. In one embodiment the term refers to organisms that cause damage to animals, including humans, or plants. The damage may relate to plant or animal health, growth, yield, reproduction or viability, and may be cosmetic damage. Preferably the damage is of commercial significance. In a preferred embodiment the term "pest" refers to organisms that cause damage to plants. Preferably the plants are cultivated plants.

BRIEF DESCRIPTION OF THE DRAWINGS

The invention will now be described with reference to the Figures in the accompany drawings in which:

Figure 2:
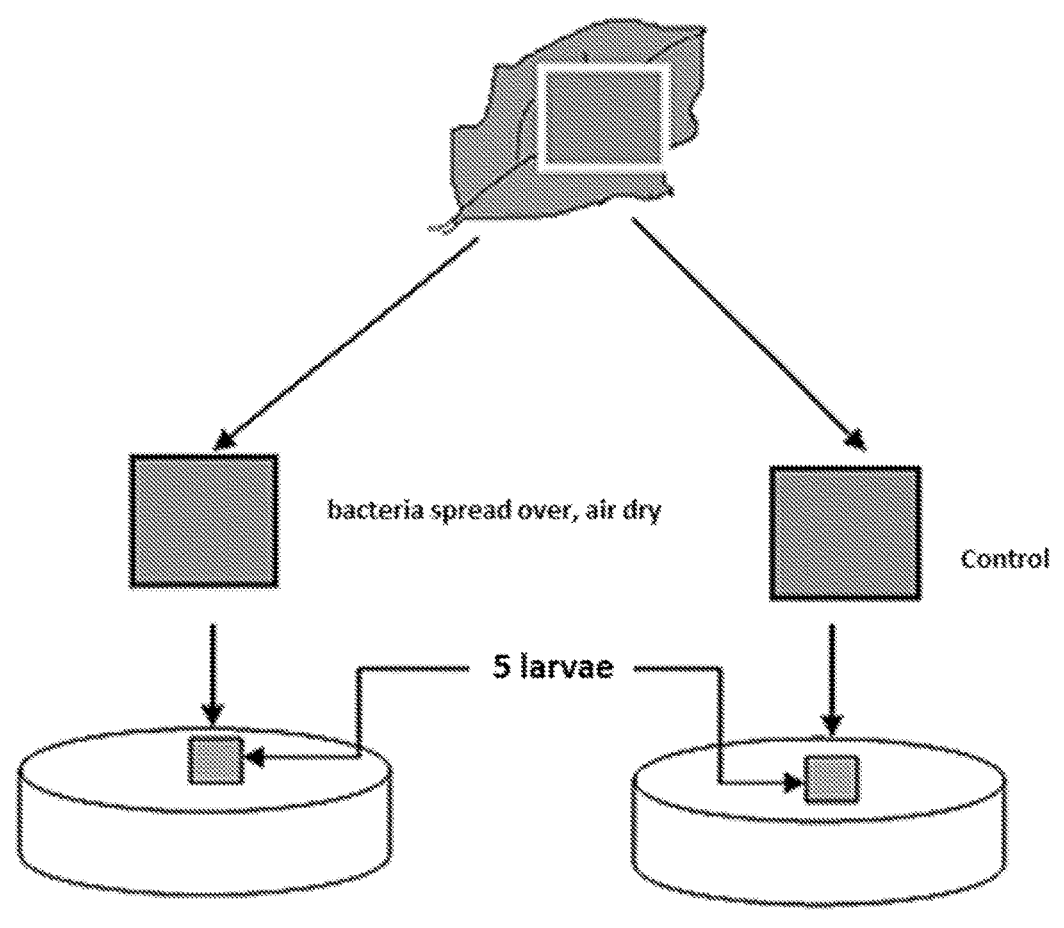

FIG. 2 shows a diagrammatic representation of the light brown apple moth assay.

Figure 7:
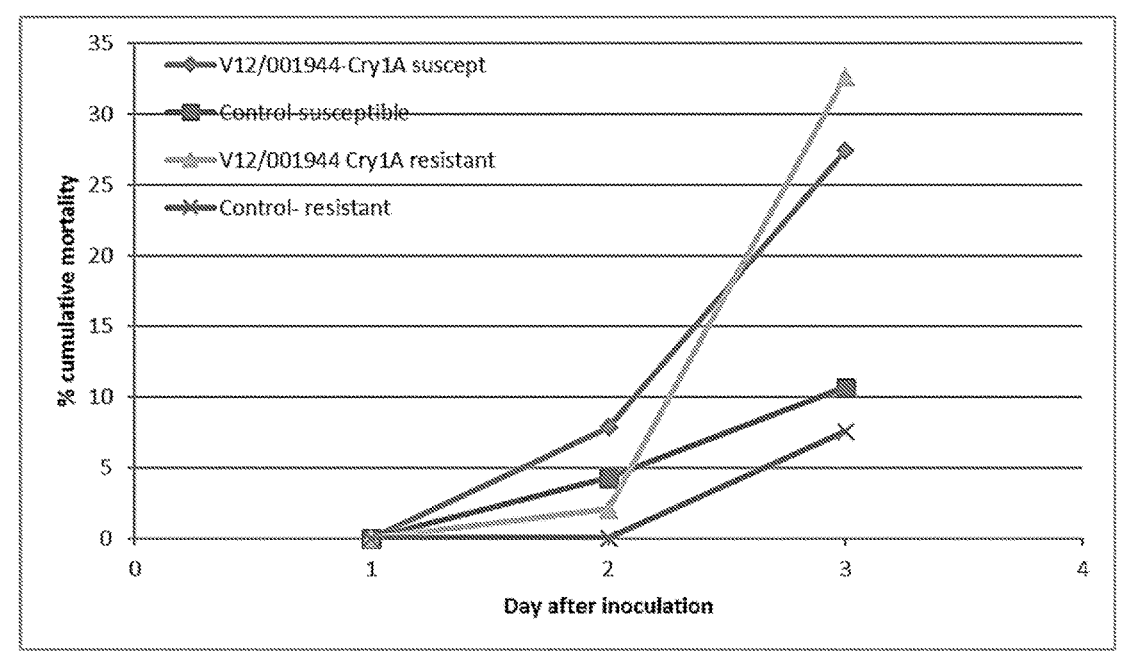

FIG. 7 shows a graph showing comparison between Cry 1A resistant *Plutella xylostella* (DBM) and susceptible to Cry1A DBM $2^{nd}$ instar larvae to weak solutions of V12/001944.

FIG. 10 shows a multiple sequence alignment of the 16s rDNA sequences used to identify each of strains NMI Nos V12/001944, V12/001945 and V12/001946, and Italian strain NCIMB41419.

DETAILED DESCRIPTION OF THE INVENTION

Figure 1:
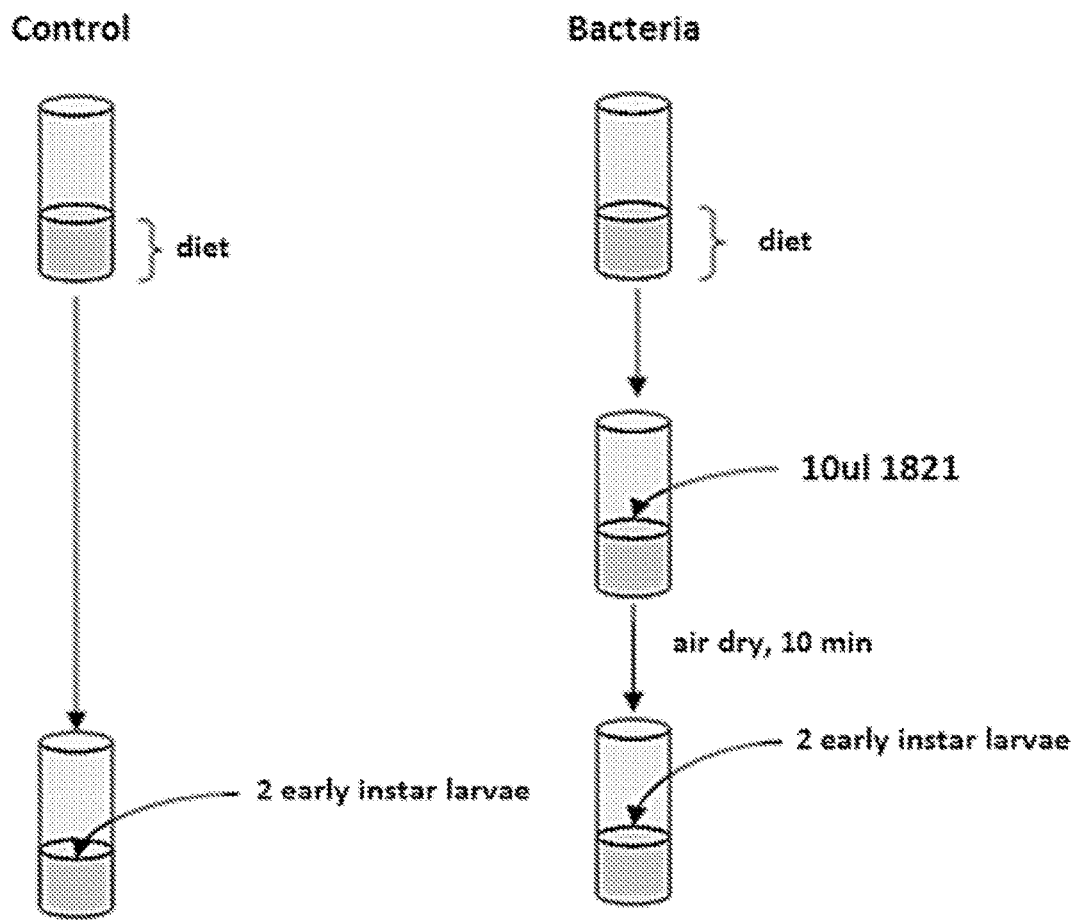
FIG. 1 shows a diagrammatic representation of a bioassay used in the host range study.

In one aspect, the present invention is directed to *Brevibacillius laterosporus* strains with activity against pests, including insect pests and particularly Lepidoptera and Diptera.

*Brevibacillus laterosporus* is an aerobic spore forming entomopathogenic bacterium, that is known to be pathogenic to some insect species. Like *Bacillus thuringiensis*, *B. laterosporus* is characterized by the formulation of a typical canoe-shaped parasporal body (CSPB) created on one side of the spore after the sporangium lysis.

*Brevibacillus laterosporus* has been recorded as a pathogen of the ova and larvae of target parasitic nematodes (Bone and Singer, 1991; Huang et al., 2005; Singer, 1996), molluscs, Coleoptera (Boets et al., 2004; Schnepf et al., 2003; Singer, 1996; Singer et al., 1997), Diptera (Favret and Yousten, 1985; Rivers et al., 1991), and the lepidopteran *Anticarsia gemmatalis* (De Oliveira et al., 2004). Different virulence factors have been recorded among the different strains of *B. laterosporus* (Favret and Yousten, 1985; Rivers et al., 1991; Zahner et al., 1999).

The association of the toxic activity of *B. laterosporus* with its spores and crystals was first demonstrated by Orlova et al. (1998) in bioassays against larvae of dipteran species, including the yellow fever mosquito *Aedes aegypti*. This mosquito serves as a vector for yellow fever and other diseases such as dengue fever and Chikungunya. Activity has also been reported against larvae of black flies (*Simulium vittatum*); mosquitoes (*Culex quinquefasciatus* and *Aedes aegypti*) (Favret and Yousten, 1985; Rivers et al., 1991); and houseflies (*Musca domestica* (Ruiu et al. 2006)), EP2,079,314.

Activity of *B. laterosporus* against Coleoptera species was first reported in preliminary bioassays. The species included the tobacco beetle *Lasioderma serricorne* and the Colorado beetle *Leptinotarsa decemlineata* (Rivers et al., 1991). Activity against the corn rootworm, *Diabratica* spp. has been reported for different strains of *B. laterosporus* (Aronson et al., 1991; Schnepf et al., 2002; Boets et al., 2011). The corn rootworm is a major agricultural pest of maize crops.

De Oliveira et al. (2004) reported high toxicity against the Mexican cotton boll weevil *Anthonomus grandis*, a pest associated with grain damage. Lepidopteran activity against the velvet bean caterpillar *Anticarsia gemmatalis* was reported in the same study.

However, there are no reports to date that discuss activity of strains against both Diptera and Lepidoptera. Rivers et al. (1991) screened 28 strains against caterpillar, mosquito and Coleoptera (potato beetles) and found no activity against caterpillar, but activity against the other two groups. Favret and Yousten (1985) also found mosquito, but not lepidopteran activity.

Surprisingly, the applicants have now identified strains of *Brevibacillius laterosporus* with activity against a range of insect pests including both some Lepidoptera and Diptera. In particular, three strains of the bacterium, *Brevibacillus laterosporus*, have been isolated from *brassica* seed and soil in New Zealand. Screening assays showed activity of all three strains against both diamondback moth larvae, *Plutella xyostella* and mosquito larvae (*Culex pervigilans* and *Opifex fuscus*).

These three new *Brevibacillius laterosporus* strains have all been deposited in the National Measurement Institute Laboratories (NMI), Suakin Street, Pymble, New South Wales, Australia on 12 Sep. 2012 according to the Budapest Treaty for the purposes of patent procedure. The isolates have been accepted for deposit under the Budapest Treaty and accorded deposit numbers NMI No. V12/001946, NMI No. V12/001945 and NMI No. V12/001944 respectively. All restrictions on the availability to the public of the material so deposited will be irrevocably removed upon grating of a patent.

Details of the isolation and selection processes employed to obtain the isolates are set out in the Examples. Identifying morphological and physiological characteristics of the *B. laterosporus* of the invention are provided in Example 3.

The applicants have been the first to provide *B. laterosporus* strains NMI No. V12/001946, NMI No. V12/001945 and NMI No. V12/001944 in isolated form.

Accordingly in one aspect, the invention provides *B. laterosporus* NMI No. V12/001946.

In another aspect, the invention provides *B. laterosporus* NMI No. V12/001945.

In another aspect, the invention provides *B. laterosporus* NMI No. V12/001944.

In one embodiment the *B. laterosporus* strains of the invention are isolated. Preferably, the strains are provided in the form of a biologically pure culture.

The strains of the invention have demonstrated insecticidal activity against a range of insect pests including both some Lepidoptera and Diptera. All three strains are the first to be provided which show this activity. More particularly, the strains are all active against both diamondback moth and mosquitoes.

Insecticidal activity has also been shown for strain NMI No. V12/001946 against a range of other insect pests including: codling moth (*Cydia pomonella*), cotton bollworm moth (*Helicoverpa armigera*), black-lyre leaf roller moth (*Cnepasia jactatana*), black legged leaf roller moth (*Planotortrix notophaea*), light brown apple moth (*Epiphyas postvittana*), manuka beetle (*Pyronota* spp) and wasp (*Vespula vulgaris*).

Activity for strains NMI No's V12/001944 and V12/001945 against cabbage looper moth (*Trichoplusia ni*) has also been demonstrated.

Strain NMI No. V12/001944 is also active against codling moth (*Cydia pomonella*).

Strains NMI No. V12/001944 and NMI No. V12/001946 also have demonstrated activity against the nematode microworm (*Panagrellus redivivus*).

The strains of the invention may have particular application against Lepidoptera Tortricidae and Lepidoptera Plutellidae families. Some activity has also been shown against Lepidoptera Noctuidae.

The insect pests discussed above are particularly problematic causing a range of issues for both plant and animal health. Moth species in particular are responsible for significant economic loss in agricultural and horticultural crops. For example, currently over US$1 billion is spent annually on diamondback moth (DBM) on control worldwide.

Mosquito control currently costs in excess of US$400 million annually.

In one embodiment the isolated *Brevibacillius laterosporus* strain of the invention has insecticidal activity against at least one Lepidoptera species and at least one Diptera species.

In one embodiment the Lepidoptera species is from a family selected from Tortricidae, Plutellidae, Nocudiae, and Geometridae.

Preferred Tortricidae species include: codling moth (*Cydia pomonella*), light brown apple moth (*Epiphyas postvittana*), blacklegged leaf roller (*Planotortrix notophaea*) and black lyre leaf roller (*Cnepasia jactatana*).

A preferred Plutellidae species is diamond back moth (*Plutella xyostella*).

Preferred Nocudiae species include cabbage looper moth (*Trichoplusia ni*) and cotton bollworm moth (*Helicoverpa armigera*).

A preferred Geometridae species is common forest looper (*Pseudocoremia suavis*)

In one embodiment the Diptera species is from the family Culcidae.

Preferred Culcidae species include *Opifex fuscus* and *Culex pervigilans*.

The present invention also provides a composition comprising at least one strain of *B. laterosporus* of the invention and an agriculturally acceptable carrier.

In one embodiment the invention provides a composition comprising at least one strain of *B. laterosporus* selected from:
 (a) *B. laterosporus* NMI No. NMI No. V12/001946
 (b) *B. laterosporus* NMI No. NMI No. V12/001945
 (c) *B. laterosporus* NMI No. NMI No. V12/001944
and an agriculturally acceptable carrier or adjuvant.

The composition may include combinations of any two or more strains of the *B. laterosporus* of the invention. That is, (a) and (b), (a) and (c) or (b) and (c). In one embodiment, the composition may comprise all three strains of the invention.

The strain(s) of the invention are present in the composition in an amount effective to control the pest of interest. The effective concentration may vary depending on the form the *B. laterosporus* is used in, the environment to which the composition is to be applied, the type, concentration and degree of pest infestation; temperature; season; humidity; stage in plant growing season; age of plant; method, rate and frequency of application; number and type of conventional fungicides, pesticides and the like being applied, and plant treatments (for example pruning, grazing, and irrigation). All factors may be taken into account in formulating the composition.

The compositions of the invention may be made by mixing one or more toxin producing *B. laterosporus* strains of the invention with a desired agricultural carrier.

Typically the product would contain fermented material of *B. laterosporus* without separation of spores and crystals, formulated for spraying. Fermented material greater than two days old, typically four days old may be used. The *B. laterosporus* in the compositions may be formulated as cell suspensions, with a desired agricultural carrier. The cells produce the insecticidal toxin either directly or via spores or crystals.

Typical concentration ranges for the *B. laterosporus*, when present in the composition in the form of intact cells, is from $1\times10^3$ to $1\times10^{14}$, preferably $1\times10^4$ to $1\times10^{10}$, more preferably $1\times10^6$ to $1\times10^8$ cells/mg. It will be appreciated that compositions with cell concentrates in order of $1\times10^{11}$ to $1\times10^{14}$ may be prepared and diluted before application if required.

*B. laterosporus* may be prepared for use in the compositions using standard drying and fermentation techniques known in the art. Growth is commonly effected under aerobic conditions in a bioreactor at suitable temperatures and pH for growth. Typical growth temperatures are from 15 to 37° C., commonly 27° C. to 32° C.

Growth medium may be any known art medium suitable for *B. laterosporus* culture. For example Nutrient Yeast Extract Salt Medium (NYSM) (Favret, and Youstein 1985).

The strains may be harvested using conventional washing, filtering or sedimentary techniques such as centrifugation, or may be harvested using a cyclone system. Harvested cells can be used immediately or stored under chilled conditions (for example at 4° C.) or may be freeze dried. Preferably cells should be used soon after harvest.

The *B. laterosporus* cells may also be processed prior to use to produce active cell extracts, cell suspensions, cell homogenates, cell lysates, cell supernatants, cell filtrates, cell pellets or may be used as whole cell preparations.

The compositions of the invention may include humectants, spreaders, stickers, stabilisers, penetrants, emulsifiers, dispersants, surfactants, buffers, binders, and other components typically employed in known art insecticidal or control compositions.

The composition of the invention may be in liquid or solid form, liquid compositions typically include water, saline or oils such as vegetable or mineral oils. Examples of vegetable oils useful in the invention are soy bean oil and coconut oil.

The compositions may be in the form of sprays, suspensions, concentrates, foams, drenches, slurries, injectables, gels, dips, pastes and the like.

Liquid compositions may be prepared by mixing the liquid agriculturally acceptable carrier with the *B. laterosporus* cells. Conventional formulation techniques may be used to produce liquid compositions.

In one embodiment the compositions is in solid form. The composition may be produced by drying the liquid composition of the invention. Alternatively, a solid composition useful in the invention may be prepared by mixing *B. laterosporus* cells of the invention with a variety of inorganic or biological materials. For example, solid inorganic agricultural carriers may include carbonates, sulphates, phosphates or silicates, pumice, lime, bentonite, or mixtures thereof. Solid biological materials may include powdered palm husks, corncob hulls, and nut shells.

The composition may be formulated as dusts, granules, seed coatings, wettable powders or the like. The compositions may be formulated before application to provide liquid compositions.

The compositions of the invention may be in the form of controlled release, or sustained release formulations.

The compositions of the invention may also include other control agents such as pesticides, insecticides, fungicides, nematocides, virucides, growth promoters, nutrients, germination promoters and the like, provided they are compatible with the function of the *B. laterosporus* strains of the invention.

Where strain(s) of the invention are used directly, the same combinations of strains, preparation and application criteria discussed above, apply.

In another aspect, the invention also provides a method for controlling pests, the method comprising contacting to the pest with a composition of the invention.

In another embodiment the invention provides a method for controlling pests, the method comprising contacting the pest with one or more *B. laterosporus* strain(s) of the invention.

In one embodiment the pest controlled by the method of the invention is selected from an insect and a nematode.

Preferred nematodes include microworms. A preferred microworm is *Panagrellus redivivus*.

In one embodiment the pest is an insect.

In one embodiment the insect is from an order selected from Lepidoptera, Diptera, Hymentoptera and Coleoptera.

In one embodiment the Lepidoptera species is from a family selected from Tortricidae, Plutellidae, Nocudiae, and Geometridae.

Preferred Tortricidae species include: codling moth (*Cydia pomonella*), light brown apple moth (*Epiphyas post-* vittana), blacklegged leaf roller (*Planotortrix notophaea*) and black lyre leaf roller (*Cnepasia jactatana*).

A preferred Plutellidae species is diamond back moth (*Plutella xyostella*).

Preferred Nocudiae species include cabbage looper moth (*Trichoplusia ni*) and cotton bollworm moth (*Helicoverpa armigera*).

A preferred Geometridae species is common forest looper (*Pseudocoremia suavis*)

In one embodiment the Diptera species is from the family Culcidae.

Preferred Culcidae species include *Opifex fuscus* and *Culex pervigilans*.

In one embodiment the Hymentoptera species is selected from the family Vespidae.

A preferred Vespidae species is the wasp *Vespula vulgaris*.

In one embodiment the Coleoptera species is selected from the family Scarabaeidae.

A preferred Scarabaeidae species is the Manuka beetle (*Pyronta* sp. A preferred *Pyronta* species is *Pyronta festiva*.

In one embodiment, a composition or strain(s) of the invention is applied directly to the pest. For example by spraying, dipping, dusting or the like.

In another embodiment, a composition or strain(s) of the invention is applied to the environment of the pest, typically on to plants or animals to be protected, equipment, ground or air. Spraying, dusting, soil soaking, seed coating, foliar spraying, misting, aerosolizing and fumigation are all possible application techniques.

In one embodiment the composition or strain(s) of the invention is applied to a plant or animal, typically on a surface, or part on which a pest feeds.

Applications may be once only or repeated as required. Application at different times in plant life cycles, are also contemplated. For example, at harvest to prevent or minimise post harvest attack by pests.

More commonly, the composition or strain(s) of the invention are applied to a plant as a seedling and at intervals at the application rates of $10^{10}$ spores/hectare to $10^{14}$ spores, preferably $10^{12}$ to $10^{13}$ spores per hectare.

Typical application rates may be 50 g/hectare to 10,000 g/hectare. Commonly from 100 g/hectare to 5,000 g/hectare, or 500 to 1500 g/hectare.

A wide range of plants may be treated using the compositions of the invention. Such plants include cereal, vegetable and arable crops, grasses, lawns, pastures, fruit trees and ornamental trees and plants.

Arable crops which may particularly benefit from use of the compositions and strain(s) of the invention include crucifers and brassicas. For example, cabbage, broccoli, cauliflower, brussel sprouts and bok choy.

When formulated for application the composition of the invention will typically be present in the formulation at a concentration of from 1 to 99% by weight, 5 to 95%, 10 to 90%, 15 to 85%, 20 to 80%, 30 to 70%, or 40 to 60% by weight.

EXAMPLES

The following non-limiting Examples are provided to illustrate the present invention and in no way limit the scope thereof.

Example 1

Process for Selection of *Brevibacillius laterosporus*

As part of a search for novel biocontrol agents of pest and diseases of brassica's, microbes were isolated from 36 seed lots of 8 *brassica* plant types, the vegetables broccoli, cabbage, kohl rabi and pak choi, and the forage plants kale, leaf turnip, rape and swede.

A total of 811 microbes were isolated onto standard microbiological media and pure cultured. They consisted of:
584 isolates of bacteria
227 isolates of fungi.

Most microbes emerged from non-sterilised seed (84%). Bacilli forming species made up 74% of all the bacterial isolates recovered, but only 2 isolates belonged to the genus *Brevibacillus*.

Bioactivity of 21 microbes (17 bacterial isolates and 4 fungi) were evaluated against diamondback moth larvae, *Plutella xylostella*, using detached leaf assay. An additional 2 bacterial species and 6 fungi from the Lincoln University culture collection were also screened for activity against *P. xylostella*. Leaf surface were contaminated with bacterial and fungal solutions and both larval feeding and mortality monitored. One *B. laterosporus* isolate was identified in this screening. A further isolate of the same species was found amongst the remaining isolates and also screened against *P. xylostella*, and showed activity.

A further isolate of *B. laterosporus* was obtained from a surface sterilised potato stolon, from an unrelated programme. It also showed activity against DBM larvae in leaf assays. These strains were subjected to further bioassays and identification confirmed.

Example 2

Isolation of *Brevibacillius laterosporus*

The three *B. laterosporus* strains were isolated from New Zealand plants or seeds. Colonies that formed on isolation plates of Nutrient Agar were selected using a sterile loop and streaked across new plates to provide a pure culture.

NMI No. NMI No. V12/001946 was isolated from hybrid cabbage seed obtained from South Pacific Seeds (NZ) Ltd.

NMI No. NMI No. V12/001945 was isolated from forage rape seed obtained from PGG Wrightson Seeds Ltd, New Zealand.

NMI No. NMI No. V12/001944 was isolated from a potato plant (cv Ilam hardy from commercial farm near Southbridge, New Zealand.

Isolation Protocols:

For the *brassica* seed, bacteria were isolated from non sterile surface of seeds onto Nutrient Agar. Individual colonies were then pure cultured.

For the potato plant, the stolon was heat treated (80° C. for 20 min) then surface sterilised (5 min in a 2% Sodium Hypochlorite solution) and tissue macerated and spread on Nutrient Agar.

Example 3

Morphological and Physiological Identification

All *B. laterosporus* isolates were identified using light microscopy to examine for characteristics of *Brevibacillius*.

Biochemical Characterisation Using API 50CH (bioMérieux).

Strains NMI No V12/001946 and NMI No. V12/001945 were further identified using the commercially available substrate utilisation kit API 50CH (bioMérieux) following the manufacturer's directions. Each was inoculated with bacteria in API 50 CHB/E medium following the manufacturer's recommendations. Identity checks from bioMérieux showed 99.9% identity with *B. laterosporus* on their database.

Morphological Characteristics

*Brevibacillus laterosporus* are aerobic, gram-positive, endospore forming bacteria which can be facultative anaerobes as well (Shida et al., 1996).

The three *B. laterosporus* NMI No's V12/001946, V12/001945 and V12/001944 have the following morphological characteristics, which are typical of the species: All three strains initially grow as vegetative cells, then form a sporangia containing a parasporal body (CSPB) and adjacent spore.

Growth Characteristics

Aerobic, facultative anaerobes; Colonies on agar are white-yellowish, irregular edged colonies.

16s rDNA Identification

The region of 16s rDNA was obtained from genome sequences of each of 4 strains of *B. laterosporus*. Genomic DNA was sequenced by the New Zealand Genomics Ltd, Dunedin, New Zealand. Contigs were searched using another 16s RDNA sequence from *B. laterosporus* and the full 16s rDNA gene extracted and aligned using the programmes Geneious (http[colon]//www[dot]geneious[dot]com/) and DNAman (Lynnon Biosoft, Canada).

SEQ ID NO. 1 was used to characterise NMI V12/001946; SEQ ID NO. 2 to characterise NMI V12/001945; SEQ ID NO. 3 to characterise NMI V12/001944 and SEQ ID NO 4. to characterise NCIMB41419. NCIMB41419 identified in EP 2,079,314 is a strain of *B. laterosporus* obtained from NCIMB Ltd, Ferguson Building, Craibstone Estate, Bucksburn, Aberdeen, AB21 9YA, Scotland.

An alignment of the sequences of SQ ID NO: 1 to 4 is shown in FIG. 10, and shows differences between each sequence, characteristic of each strain.

Example 4

Bioassay Procedures

Diamondback Moth (*Plutella xylostella*) (Lepidoptera: Plutellidae), Cabbage White Butterfly *Pieris rapae* (Lepidoptera: Pieridae) and Cabbage Looper Moth (*Trichoplusia ni*) (Lepidoptera: Noctuidae)

Diamondback moth larvae were reared on *brassica* (cabbage plants) at Lincoln, or the strains resistant to Cry1A and Cry1C and a susceptible (G88) strain were obtained and tested at the New York State Agricultural Experiment Station, College of Agriculture and Life Sciences at Cornell University, located in Geneva, N.Y., USA. Cabbage white butterfly larvae were field collected from the farm at Lincoln University, New Zealand.

Ten $2^{nd}$-$3^{rd}$ instar larvae were used and placed on 3 cm disc of cabbage leaf treated with either 20 μl of bacteria-containing strains (NMI No's: V12/00944, V12/001945 or V12/001946) solution, or dipped in the solution. An Italian strain of *B. laterosporus*, NCIMB41419, and a culture of another bacterial genus, *Erwina* (ICMP) were also used as comparisons against DBM larvae. A wetting agent, Siliwet L-77 (Momentive Performance Materials, New York, USA) or Triton X-100 (Rohm and Hass Co, Philidelphia, USA) was used at <0.05%. Each treatment was replicated 3-5 times (3-50 larvae per treatment). Treated larvae remained on the cabbage leaf at 23° C. 16L:8HD (Lincoln) or at 27° C. 16hL:8hD (USA) and were checked daily for dead.

Susceptible and Cry1A resistant *Trichoplusia ni* were also obtained and tested at the New York State Agricultural Experiment Station, College of Agriculture and Life Sciences at Cornell University, located in Geneva, N.Y., USA. Second-$3^{rd}$ instar larvae were inoculated and maintained as for DBM, except only 5 larvae were used per replicate (a total of 25 larvae per treatment). Larvae were maintained at 27° C. 16hL:8hD after treatment.

Codling Moth (*Cydia pomonella*) Bioassay (Lepidoptera: Tortricidae)

The bioassay was set up using the codling moth larvae from eggs provided by Plant and Food Research Center, (PFR), Auckland, New Zealand. PFR also supplied the artificial diet used in the rearing of the insect.

Preliminary and confirmatory tests were done to evaluate the reaction of the insect to NMI NO. V12/001946. Each bioassay had two treatments consisting of a) diet treated with NMI No. V12/001946 or V12/001944 full strength (4 day old shaker flask material grown in NYSM at 30° C. used undiluted, with 0.025% contact used as a wetting agent) and b) untreated diet as control. In the preliminary set up, each treatment was replicated 10 times with 1 tube representing a replicate. For the confirmatory test, each treatment had 30 replicates or 1 tube as replicate. For the treated diet, 10 μl of NMI No. V12/001946 was spread over the surface and allowed to air dry for 10 min. Two $2^{nd}$ instar larvae were introduced into each tube and tubes were covered with parafilm.

All tubes were placed in a rack and put in the incubator at 25° C. and photoperiod of 16:8 (L:D). Larval mortality was observed daily with the initial data gathered 1 day after inoculation.

Housefly (*Musca domestica*) Bioassay (Diptera: Muscidae)

The bioassay trial was conducted using the larvae (maggots) and pupa purchased from Biosuppliers Insects, a company which supplies live insects (www[dot]biosuppliers[dot]com) based in Auckland, New Zealand. The artificial diet by Ruiu et al. 2006 was used in the set-up.

The reaction of NMI No. V12/001946 against maggots and pupa was observed in two treatments, a) diet treated with full strength NMI No. V12/001946 and b) untreated diet as control. In the preliminary set-up using maggots each treatment had three pottel cups (Huhtamaki Co., Henderson, Auckland, New Zealand) with 10 ml of the diet. For the treated diet, 200 μl of NMI No. V12/001946 full strength was thoroughly mixed with the diet before introduction of six maggots. In the set-up using pupa, each treatment had one pottel with five pupae placed in each cup.

The set up was placed in the incubator at 21° C. and photoperiod of 16:8 (L:D). Daily observation of the set up was done.

Common Forest Looper Moth (*Pseudocoremia suavis*) Bioassay (Lepidoptera: Geometridae)

The eggs of common forest lopper were supplied by PFR. The eggs were allowed to hatch in one of the Controlled Temperature (CT) rooms at the Bioprotection Center, Lincoln, New Zealand with 20° C. and 16:8 (L:D) photoperiod. Emerging larvae were then reared in detached radiata pine shoots grown at the Lincoln University Nursery, Lincoln, New Zealand. The shoots were washed thoroughly, patted dry and placed in a plastic container lined with moist paper towel. The container was covered with meshed lids to allow aeration. Fresh pine leaves were supplied daily until larvae reached the $3^{rd}$ instar for bioassay.

There were two bioassays done using leaf dip method. Each bioassay had two treatments as follows: a) radiata pine leaves dipped in bacteria with 0.01% Triton X 100 (wetting agent, Rohm and Haas Co. Philadelphia, USA) and b) the control, leaves dipped in sterile distilled water with 0.01% Triton X-100. Each treatment has 2 leaf samples representing 2 replications. In the $1^{st}$ bioassay, $10^{-1}$ bacterial dilution was used while the $2^{nd}$ trial utilized full strength. The leaves were allowed to air dry before 5 larvae were introduced into the leaves. The set-up was placed in the CT room with 20° C. and 16:8 (L:D) photoperiod.

Grass Grub [*Costelytra zealandica*] Bioassay (Coleoptera: Scarabaeidae)

The larvae of grass grub were collected from nearby field. Prior to bioassay, the larvae were pre-fed with carrots cubes in a 12-well tissue culture plates. Refeeding with fresh carrot cubes was done as needed. After 2 days, all actively eating larvae were selected for the bioassay.

The bioassay had two treatments namely, carrot cubes treated with NMI No. V12/001946 and control, untreated carrot cubes. For the NMI No. V12/001946 treated carrot cubes, each cube was rolled over NMI No. V12/001946 grown in nutrient agar for 2 days. Twelve wells were assigned per treatment with 1 larva per well. The plates were placed in a tray lined with moist paper towel and enclosed with a clear plastic bag to increase humidity and prevent drying of the carrot cubes. The tray was placed in the incubator at 21° C. and 16:8 (L:D) photoperiod. Daily observation was done.

Manuka Beetle (*Pyronota* spp.) Bioassay (Coleoptera: Scarabaeidae)

Two bioassays were done involving larvae of Manuka beetle, carrot cube bioassay and soil bioassay. The larvae of the Manuka beetle were provided by Landcare Farming Ltd, Westport, New Zealand.

For the carrot cube bioassay, the same steps as that in the grass grub were followed. In the soil bioassay, the larvae were pre-fed with carrot cubes for 2 days in 12-well tissue culture plates. Actively eating larvae were selected for the bioassay. Ten grams of sterilized soil were placed in universal bottle. Two ml of sterile distilled water were pipetted into the soil and mixed well. Treated soil had 500 ml of NMI No. V12/001946 full strength mixed thoroughly with the soil. Control had only 2 ml of sterile distilled water mixed in the soil. One larva was introduced in each bottle and was fed with 1 carrot cube. The lid of the bottles were loosely closed and placed in incubator at 21° C. and 16:8 (L:D) photoperiod. Daily observation of larval mortality was done.

Light Brown Apple Moth (LBAM) (*Epiphyas postvittana*) Bioassay (Lepidoptera: Tortricidae)

The bioassay was based on the work of Wearing et al. (2003) with modifications. Their method used fully expanded apple leaves with the larvae transferred to new leaves every week until $4^{th}$ instar. The leaf was placed flat with abaxial side down. Young apple leaves from the BHU, Lincoln University, and larvae of LBAM from eggs kindly supplied by Plant & Food Research were used for the set up.

In the preliminary bioassay, modifications from the Wearing et al. (2003) protocol was done as follows: 1) instead of whole leaf, the leaf was cut into one square inch 2) two leaf orientation were used 3) larvae were not transferred into new leaf.

The preliminary bioassay had two treatments: untreated leaves as control and leaves treated with 1821 full strength. One square inch of leaf was cut from a young well expanded leaf. For the treated leaf sample, 40 µl of V12/001946 full strength was spread over the surface and allowed to air dry. The control and treated leaf samples were placed on the surface of water agar in 2 ways: 1) abaxial (lower) side of the leaf in contact with the agar and adaxial (upper) side in contact with the agar. There were 2 leaf samples per treatment and per leaf orientation. Five larvae were placed in each leaf sample.

A second bioassay was done using whole leaf method. Treatments and procedures were the same as that in the first bioassay.

Tomato Fruitworm Moth (aka Corn Earworm and Common Bollworm Moth) (*Helicoverpa armigera*) Bioassay (Lepidoptera: Noctuidae)

The reaction of V12/001946 against tomato fruitworm was evaluated in a bioassay using larvae from eggs kindly provided by PFR and artificial diet based on Singh (1983) with modifications. The modifications were that preservative, antibiotic and anti-fungal chemicals were not incorporated in the diet.

The bioassay had two treatments: diet treated with V12/001946 full strength and untreated diet as control. Six portion cups (Huhtamaki Co., Henderson, Auckland) with 5 ml of the diet were used per treatment. In the treated diet, 20 µl of V12/001946 full strength was spread over the surface of the diet and allowed to air dry. Five larvae were introduced per cup in the treated and untreated diets. The cup was covered with parafilm to prevent drying of the diet. Treated and untreated cups were placed in incubator with 25° C. and 16:8 (L:D) photoperiod.

Mosquito Bioassay (*Culex pervigilans* and *Opifex fuscus*) (Diptera: Culicidae)

The bioassay was done using larvae of mosquitoes (both species) collected by Lincoln University from a disused swimming pool (*Culex pervigilans*) in Oxford, Canterbury, New Zealand or supplied (*Culex pervigilans* and *opifex fuscus*) by New Zealand BioSecure Entomology Laboratory Research, Lincoln, Christchurch. The assay had seven treatments namely, NMI No. V12/001946 full strength (from shaker flask), 5 bacterial dilutions of $10^{-2}$, $10^{-4}$, $10^{-6}$, $10^{-8}$, $10^{-10}$ and untreated larvae as control. Each treatment had 12 wells representing 12 replications and laid out in a completely randomized design.

One ml of water and 1 larva was pipetted into each well of the 12-well tissue culture plate. For the treated larvae, 20 µl of NMI No. V12/001946 was introduced into each well. The plates were covered with lids and placed in incubator at 25° C. and 16:8 (L:D) photoperiod. Larval mortality as indicated by absence of larval movement when gently shake was assessed daily.

The assay was repeated using the three strains, NMI V12/001944, V12/001945 and V12/001946, an Italian strain of *B. laterosporus*, NCIMB41419, and a culture of another bacterial genus, *Erwina* (ICMP) were also used as comparisons.

Tropical Army Worm Moth (*Spodoptera litura*) Bioassay (Lepidoptera: Noctuidae)

The larvae used in the bioassay were hatched from eggs supplied by PFR. A day after emergence, the larvae were reared overnight in the artificial diet developed for tomato fruitworm. The diet proved to be appropriate as well for the tropical army worm as shown by presence of excreta on the surface of the diet.

There were two treatments in the bioassay, diet treated with full strength NMI No. V12/001946 and the untreated diet as control. Each treatment has 6 pottel cups representing 6 replications. Twenty (20) μl of the bacteria was spread over the surface of the diet and allowed to air dry. Five larvae were introduced in each pottel cup. The cup was covered with parafilm after larval introduction.

The set up was placed inside the incubator with 25° C. and 16:8 (L:D) photoperiod. Larval mortality was observed daily.

Blacklegged Leaf Roller Moth (*Planotortrix notophaea*) and Black Lyre Leaf Roller Moth (*Cnephasia jactatana*) Bioassays (Lepidoptera: Tortricidae)

The test insects and the artificial diet for two bioassays were provided by PFR. A day after emergence from eggs, the larvae were reared overnight in the artificial diet and placed in incubator with 21° C. and 16:8 (L:D) photoperiod.

Both bioassays had two treatments, diet treated with full strength of NMI No. V12/001946 and the untreated diet as control. In the bioassay involving blacklegged leaf roller, the control had 15 tubes, each tube representing a replicate while the treated diet had 14 replicates. For the black lyre bioassay, the treated and untreated diets had 15 replicates each. Two $2^{nd}$ instar larvae were introduced into each tube and were covered with parafilm.

The treated and untreated tubes in both bioassays were placed in incubator with 21° C. and 16:8 (L:D) photoperiod. Larval mortality was observed daily under stereo microscope. Absence of larval movement when slightly brushed off by camel brush was rated dead.

Mealyworm (*Tenebrio molitor*) Bioassay (Coleoptera: Tenebrionidae)

The larvae and the diet for the bioassay were purchased from Biosuppliers Live Insects, Auckland, New Zealand. There were two treatments, diet treated with NMI No. V12/001946 full strength and the untreated diet as control. Each treatment has 2 replications with 1 container as replicate.

Two hundred fifty mg of the diet were placed into each container. For the treated diet, 200 µl were mixed thoroughly with the diet and allowed to air dry. The same amount of sterile distilled water was mixed with the diet in the control. Five larvae were placed into each container and covered with lid which has a hole punched in the center. The containers were then placed in the incubator with 25° C. and 16:8 (L:D) photoperiod.

Sour Paste Nematode/Microworms (*Panagrellus redivivus*) Bioassay (Nematoda: Rhabditida)

The free living nematode was purchased from Biosuppliers. There were two bioassays completed to test the reaction of the *B. laterosporus* bacteria against microworm. For the two bioassays, microworms were provided in a paste form and were scooped out of the paste and placed in deep petri dish with sterile distilled water to allow separation of individual nematodes. A one ml pipette tip with the tip cut was used to get individual microworms into the sterile distilled water.

There were three treatments in the first bioassay: 1) microworms treated with V12/001946 full strength, 2) microworms treated with V12/001944 full strength and 3) untreated microworms as control. Ten microworms were placed in each well of the 12-well tissue culture plates. One ml of sterile distilled water was placed in each well. Each treatment has 6 replicate wells which were laid out in completely randomized design. In the treated microworms, 10 μl of bacteria was added per well. The bioassay was at room temperature.

The microworm mortality was assessed daily until three days after inoculation. Larval mortality was observed under the stereo microscope.

In the second bioassay, bacterial broth was used instead of the centrifuged material. There were five treatments evaluated namely, 1) V12/001944 full strength broth, 2) $10^{-2}$ dilution 3) $10^{-3}$ dilution, 4) $10^{-4}$ dilution and 5) untreated as control. There were ten microworms per well with six wells per treatment laid out in completely randomized design. For the treated microworms, 20 μl of bacterial broth was added per well. The bioassay was also completed at room temperature.

The mortality was assessed daily until three days after inoculation. Larval mortality was observed under the stereo microscope.

Argentine Stem Weevil (*Listronotus bonariensis*) (Coleoptera: Curculionidae)

Two bioassays were conducted to assess the reaction of V12/001946 against the Argentine stem weevil. The test materials for both bioassays, ryegrass and the weevil were from field collected material, Canterbury, New Zealand.

The initial bioassay had two treatments: 1) ryegrass treated with V12/001946 full strength broth and untreated leaves as control. The rye grass was cut into 2-inch length. For the V12/001946 treated grass, the grass sample was dipped in V12/001946 full strength broth and allowed to air dry for 10-15 minutes. The control and treated grass samples were placed in a petri dish. There were five Petri dish in the treated grass and four in the control. Ten weevils were placed in each grass sample. The petri dish was then sealed with wrapping film. All petri dish were placed inside the incubator with 22° C. and 12:12 (L/D) photoperiod. Larval mortality was observed daily.

The second bioassay utilized whole rye grass seedlings. Three week-old ryegrass seedlings were used. The roots of the ryegrass seedlings were placed in a small plastic bag and enough water was placed to prevent drying up of the seedling. The plastic bag was fastened just above the roots with a plastic zipper tie to prevent water from coming out of the bag.

The bioassay had two treatments as follows: 1) V12/001946 treated rye grass and untreated rye grass as control. There were three rye grass seedlings per treatment. For the untreated rye grass, 500 μl of sterile distilled water were sprayed into each seedling using an air brush. In the treated rye grass, 500 μl of V12/001946 broth were sprayed. The seedlings were allowed to air dry after spraying and placed in a rectangular plastic container with a meshed lid. Ten weevils were introduced into each seedling. All containers were placed in the incubator at 22° C. and 12:12 (L/D) photoperiod. Daily assessment of larval mortality was done.

Waterboatmen (Hemiptera: Corixidae)

The bioassay was done using the waterboatmen field collected from Oxford, New Zealand. There were two treatments: 1) V12/001946 treated waterboatmen and untreated as control. One waterboatman was placed in a universal bottle with 5 ml of sterile distilled water. There were five bottles per treatment. In the treated waterboatmen, 40 μl of full strength V12/001946 was added to the sterile distilled water. The experiment was done at room temperature (20-24° C.). Mortality was assessed daily.

Diving Beetle (*Antiporus duplex*) (Coleoptera: Dytiscidae)

The diving beetle used in the bioassay were field collected at Oxford, New Zealand. The bioassay has two treatments namely, 1) V12/001946 treated diving beetle and untreated as control.

Twelve-well tissue culture plates was utilized in the bioassay. One diving beetle was placed per well with 6 wells per treatment. Two ml of sterile water were placed in each well. For the V12/001946 treated diving beetle, 10 μl of V12/001946 full strength was added. The bioassay was done at room temperature (20-24° C.) with daily recording of mortality.

Common Wasp *Vespula vulgaris* Adults (Hymenoptera: Vespidae)

The bioassay was done using wasp adults collected from flowering plants around Lincoln University. Two treatments were evaluated: V12/001946 treated wasp and untreated as control. Five wasps were placed in a plastic container with lid punched with small holes.

The wasps in the control were fed with 2 ml of 10% sucrose solution placed in a small plastic lid. For the V12/001946 treated wasps, 2 ml of 10% sucrose was mixed with 1 ml of V12/001946 full strength (concentrated). Sucrose solutions (with and without V12/001946) were placed prior to introduction of wasps into each container.

The bioassay was done at room temperature (20-24° C.). Mortality was recorded daily.

Three New Zealand isolates of *B. laterosporus* (NMI No's V12/001944, V12/001945 and V12/001946) showed activity against DBM larvae (see FIG. 3). Against a range of other Lepidoptera, the bacteria were toxic against some species. (Table 1). The leafrollers (blacklegged leafroller, black lyre leafroller, light brown apple moth all Tortricidae), codling moth (Tortricidae) and DBM (Plutellidae) and a Noctuidae were susceptible.

Figure 4:
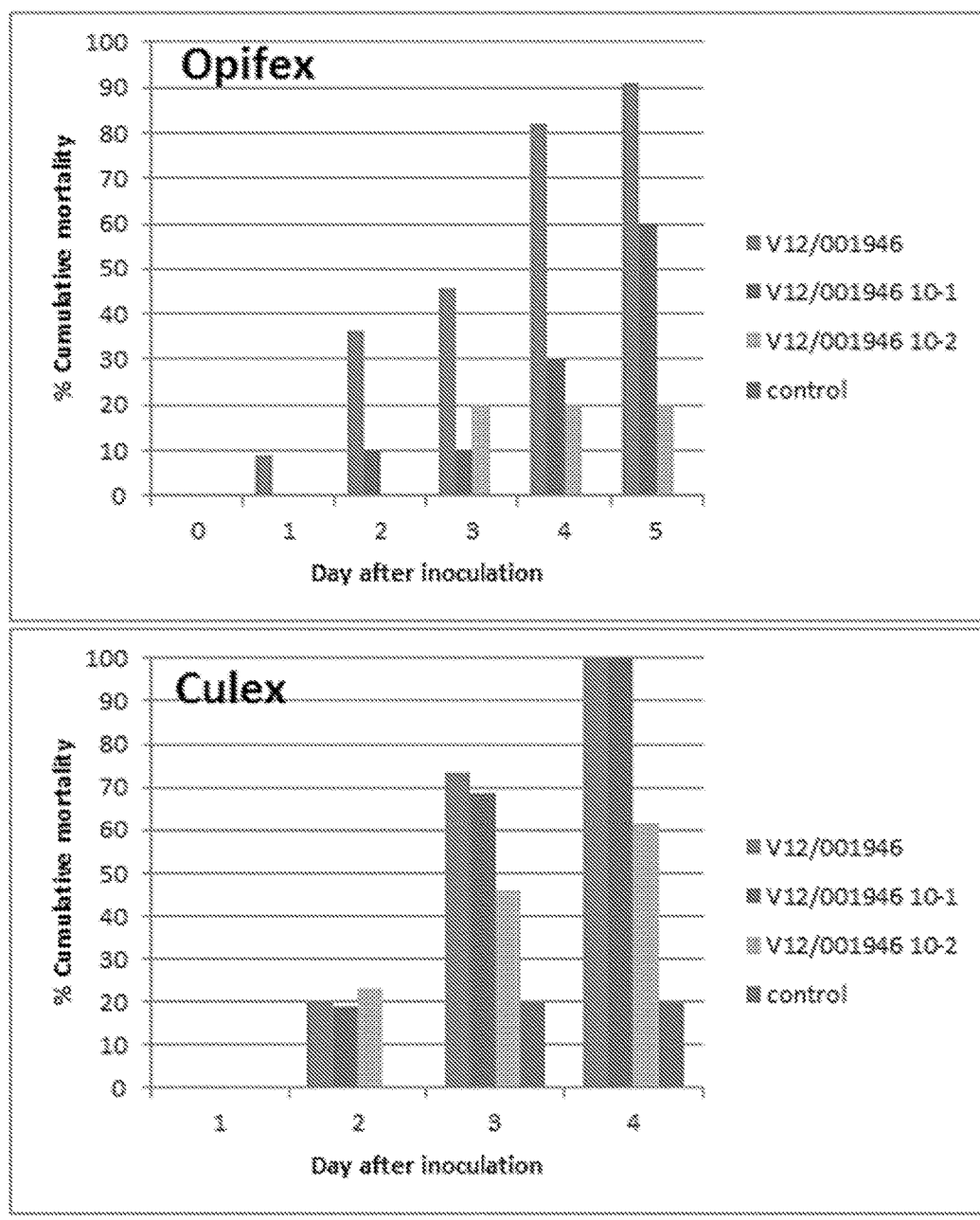
FIG. 4 shows a bar graph showing activity of *B. laterosporus* strain NMI No. V12/001946 against the mosquitoes *Culex pervigilans* and *Opifex fuscus*. Treatments were isolate NMI No. V12/001946=500 μl in 10 ml, NMI No. V12/001946=50 μl in 10 ml and NMI No. V12/001946 (1821-2)=5 μl in 10 ml (500 ppm).
Figure 5:
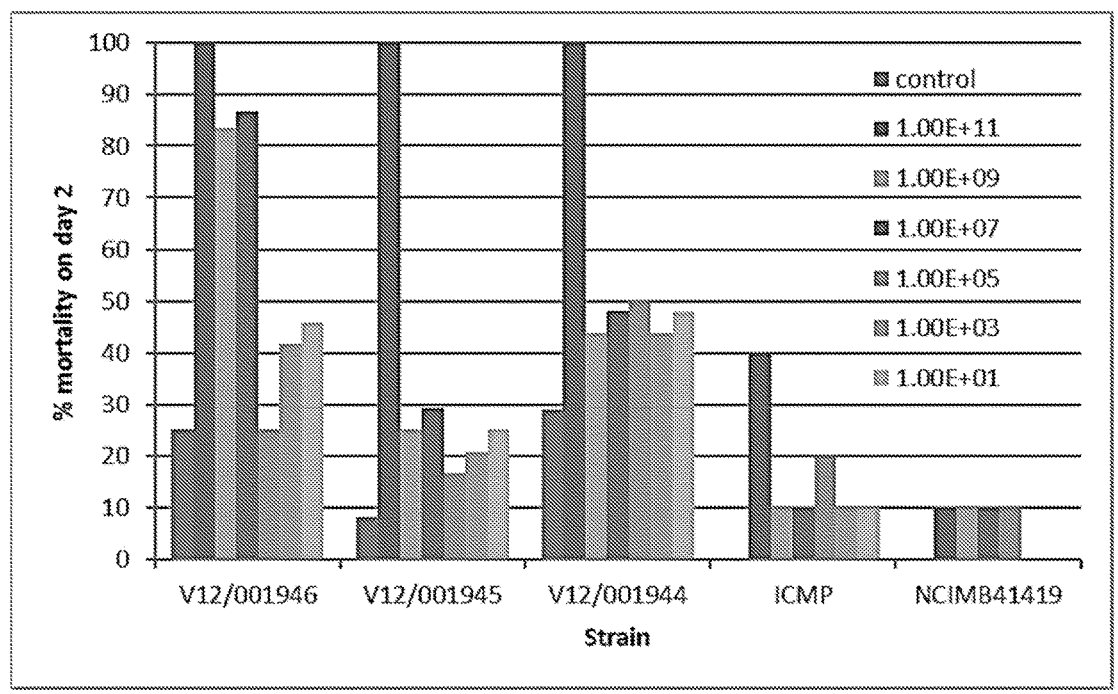
FIG. 5 shows a bar graph showing percentage mortality of *Culex pervigilans* mosquito inoculated with 20 μl of bacterial suspension NMI No. V12/001946, NMI No. V12/001945 and NMI No. V12/001944, ICMP or NCIMB41419 in 1 ml of water for each mosquito larvae. 12 larvae were individually treated for each dilution.
Figure 6:
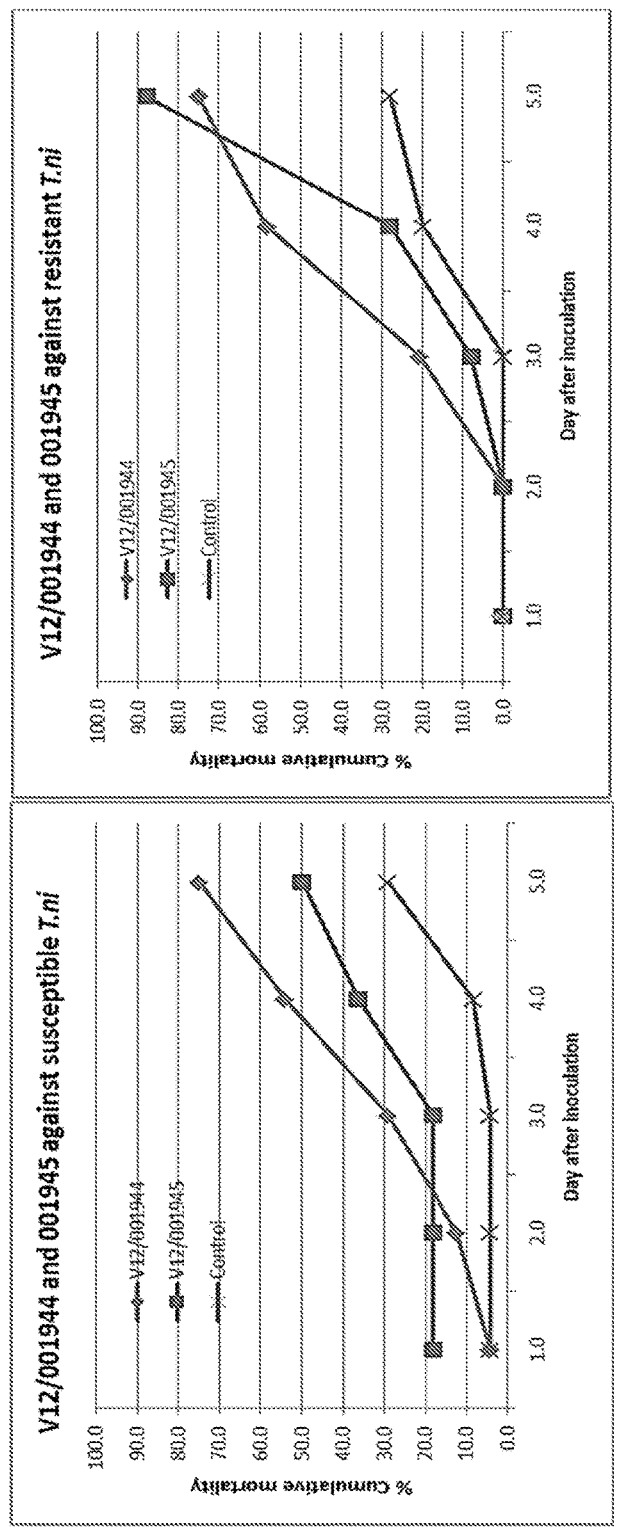
FIG. 6 shows a graph showing the effect of NMI No. V12/001944 and V12/001945 on Bt Cry1A resistant (FIG. 6A) and susceptible (FIG. 6B) cabbage looper *Trichoplusia ni*.
Figure 8:
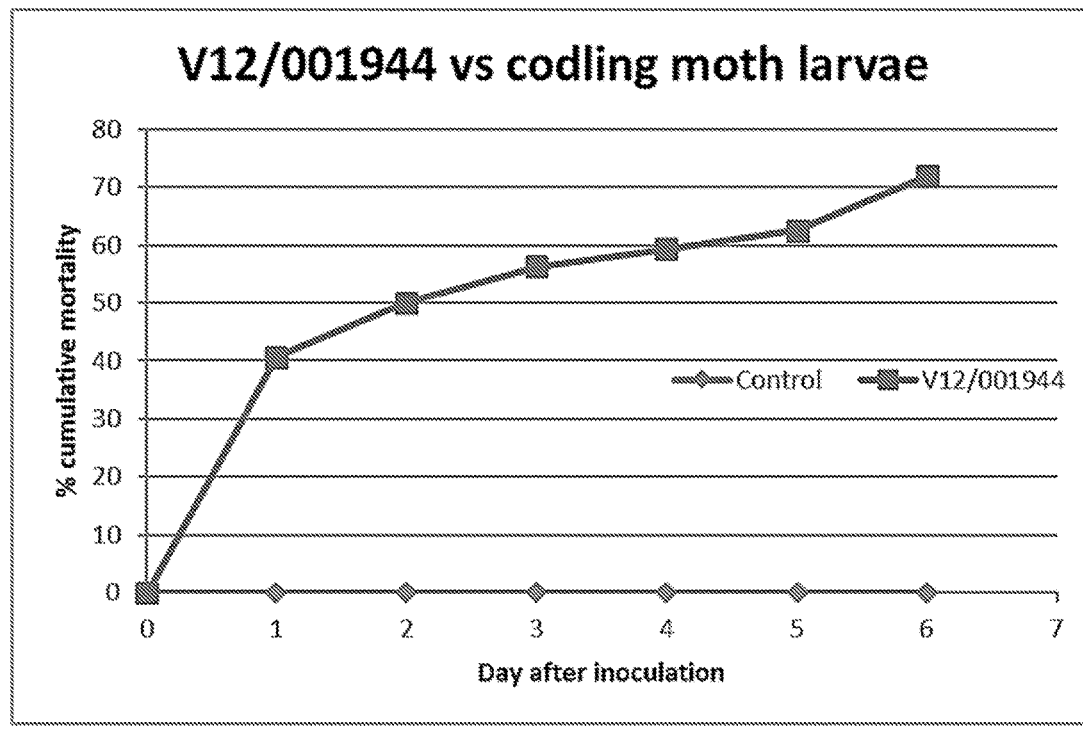
FIG. 8 shows a graph showing the effect of NMI No. V12/001944 on codling moth larvae.

Mosquitoes (Diptera: Culicidae) are also very susceptible to the bacteria (FIGS. 4 and 5). There is some susceptibility in the Manuka beetle (a scarab), but this was not seen when the larvae were inoculated in soil. Grass grub, another scarab, were not susceptible (Table 2). Hymenopteran wasps, *Vespula vulgaris* adults appear to be susceptible.

Figure 9:
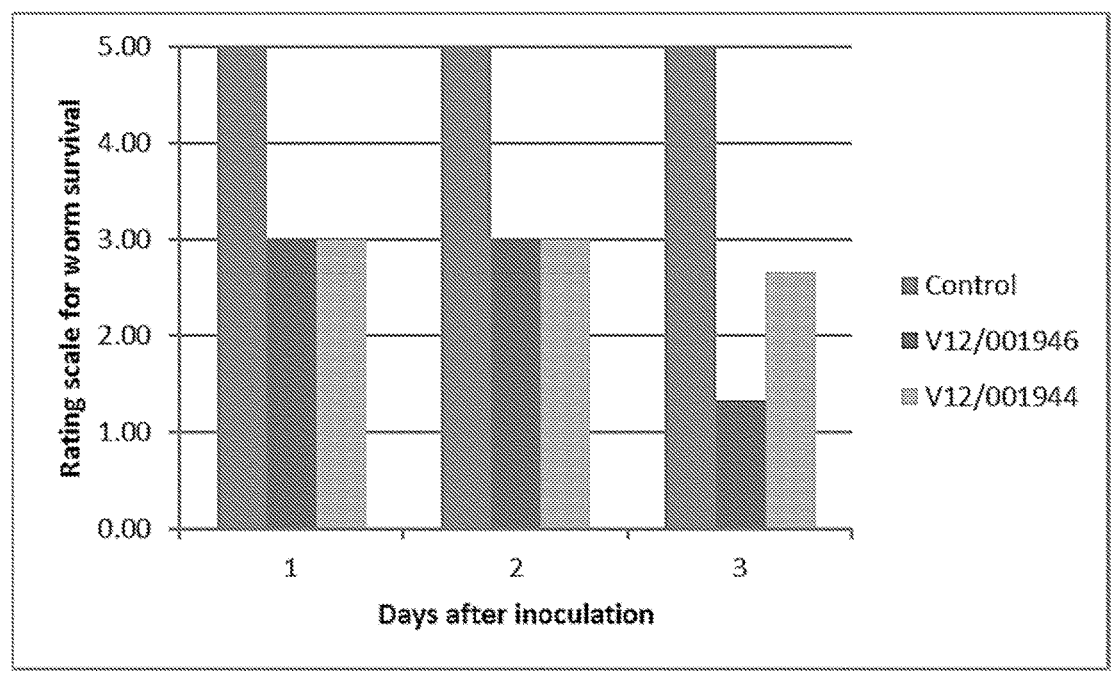
FIG. 9 shows a bar graph showing survival of microworms (*Panagrellus redivivus*) treated with V12/001946 and V12/001944. Rating is a scale out of 5 for number alive.

Nematode activity was demonstrated against a species of nematodes, known as Microworms (*Panagrellus redivivus*) (FIG. 9).

Figure 3:
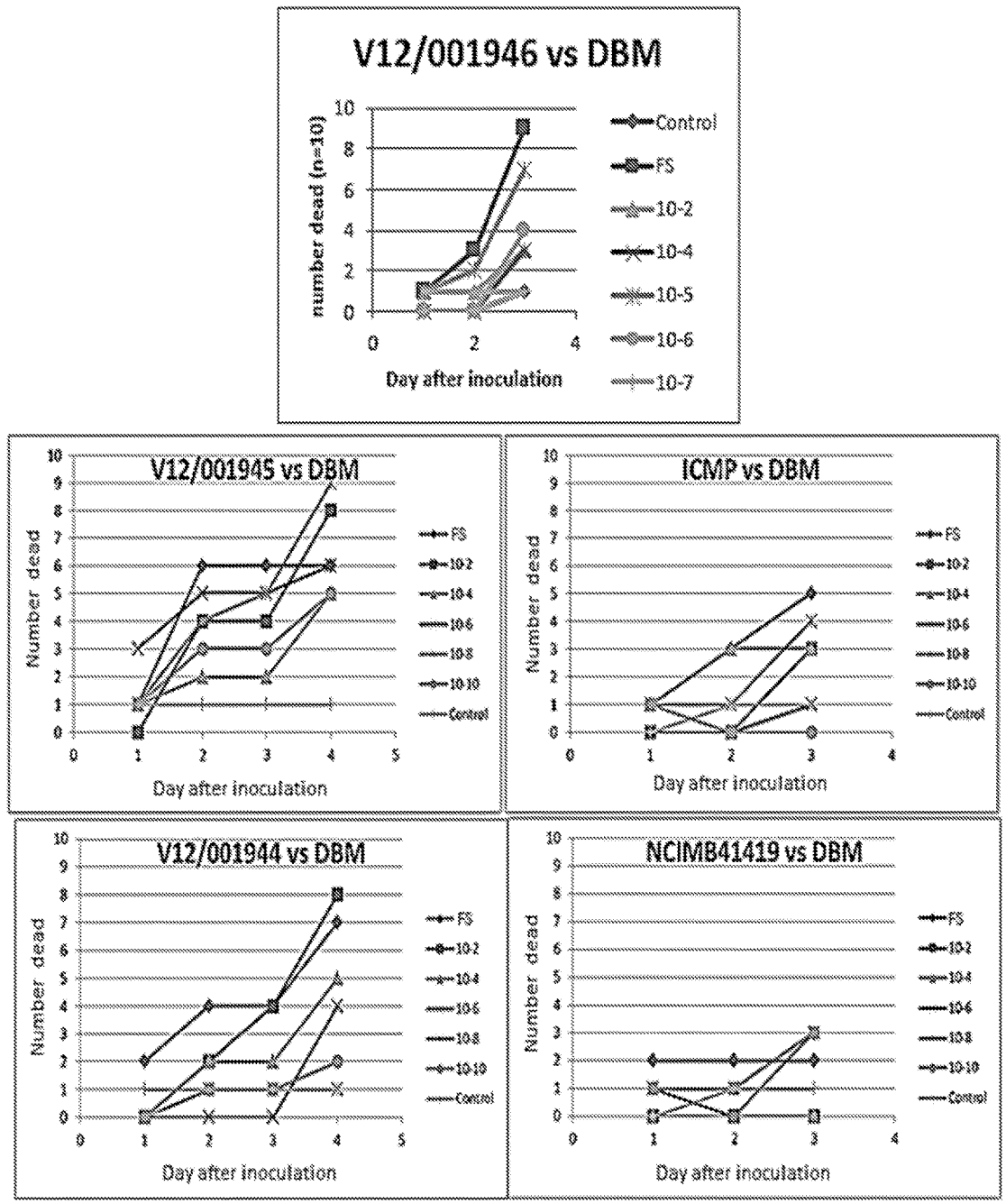
FIG. 3 shows series of graphs showing comparative activity of *B. laterosporus* strains NMI No. V12/0001946, NMI No. V12/0001945 and NMI No. V12/0001944; and an Italian strain *B. laterosporus* NCIMB41419 and an *Erwinia* sp. (ICMP) against diamondback moth (*Plutella xyostella*) larvae (n=10, 22° C.).

*B. laterosporus* strain NCIMB 41419 was not effective against diamondback moth (FIG. 3) or against mosquito (FIG. 5).

TABLE 1

Summary of bioassays against lepidopteran insects using strain V12/001946. (Full strength is approximately $10^{10}$ cells/ml of a 3-4 day old culture)/

| Treatment and species | Dilution | % mortality | N |
|---|---|---|---|
| *Cydia pomonella* (codling moth) (Tortricidae) | | | |
| Control | — | 16.7 | n = 30 |
| V12/001946 | $10^{-4}$ | 66.7 | |
| V12/001946 | $10^{-2}$ | 83.3 | |
| V12/001946 | 0 | 73.3 | |
| *Helicoverpa armigera* (cotton bollworm/corn earworm/tomato fruit worm) (Noctuidae) | | | |
| Control | — | 3.3 | n = 30 |
| V12/001946 | 0 | 0.0 | |
| *Pseudocoremia suavis* (pine looper/common forest looper) (Geometridae) | | | |
| Control | — | 0.0 | n = 20 |
| V12/001946 | 0 | 5.0 | |

TABLE 1-continued

Summary of bioassays against lepidopteran insects using strain V12/001946. (Full strength is approximately $10^{10}$ cells/ml of a 3-4 day old culture)/

| Treatment and species | Dilution | % mortality | N |
|---|---|---|---|
| (25 day-old) V12/001946 | 0 | 10.0 | |
| (4-day old) | | | |
| *Cnephasia jactatana* (black-lyre leafroller moth) (Tortricidae) | | | |
| Control | — | 36.7 | n = 30 |
| V12/001946 | 0 | 83.3 | |
| Control | | 23.3 | |
| V12/001946 | $10^{-4}$ | 50.0 | n = 30 |
| V12/001946 | $10^{-2}$ | 50.0 | |
| V12/001946 | 0 | 76.7 | |
| *Planotortrix notophaea* (blacklegged leafroller) (Tortricidae) | | | |
| Control | | 30.0 | n = 10 |
| V12/001946 | 0 | 40.0 | |
| Control | | 36.7 | n = 30 |
| V12/001946 | 0 | 50.0 | |
| Control | | 21.4 | n = 28 |
| V12/001946 | 0 | 39.3 | |
| *Epiphyas postvittana* (lightbrown apple moth) (Tortricidae) | | | |
| Control | | 30 | n = 10 |
| V12/001946 | 0 | 60 | |
| *Spodoptera litura* (Tobacco cutworm/armyworm) (Noctuidae) | | | |
| Control | | 10.0 | n = 30 |
| V12/001946 | 0 | 0.0 | |
| *Pieris rapae* (cabbage white butterfly) (Pieridae) | | | |
| Control | | 0 | n = 10 |
| V12/001946 | 0 | 0 | |
| Dipel (positive control) | 0 | 100 | |

TABLE 2

Other species

| Treatment and species | Dilution | % mortality | Comment |
|---|---|---|---|
| Water boatmen (Corixidae) | 0 | not susceptible | |
| Diving beetle (*Antiporus duplex*) | | not susceptible | |
| Grass grub, *Costelytra zealandica* | | not susceptible | |
| Manuka beetle, *Pyronta* sp.- | | 7/20 dead after 24 days using carrot inoculation. | None dead when treated in soil |
| *Vespula vulgaris* adults (common wasp) | Control - 2 ml 10% sucrose | 3/5 | |
| | 1 ml Full strength (FS) (centrifuged) + 1 ml 10% sucrose | 5/5 | 5/5 dead after 1 day (1/5 for control) |
| Argentine stem weevil (*Listronotus bonariensis*) (*Coleoptera*: *Curculionidae*) | Control | 0/60 | not susceptible |
| | V12/001946 | 1/60 | |
| *Musca domestica* (housefly) | Control | 1/16 | |
| | V12/001946 | 3/16 | |

The three strains of *B. laterosporus* isolated from New Zealand plants have all shown activity against some lepidopterans and dipterans. Within the Lepidoptera, all the Tortricidae and Plutellidae species tested were susceptible. Within Diptera mosquitoes were susceptible.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

REFERENCE LISTING

Aronson, A. I., & Dunn, P. E. (1991). U.S. Pat. No. 5,055, 293.

Baxter, S. W., Badenes-Pérez, F. R., Morrison, A., Vogel, H., Crickmore, N., Kain, W., Wang, P., Heckel, D. G. and Jiggins, C. D. (2011) Parallel evolution of *Bacillus thuringiensis* toxin resistance in Lepidoptera. *Genetics October*, 189, 675-679.

Boets, A., Arnaut, G., van Rie, J., & Damme, N. (2011). Belgium Patent No. US 7919609B2.

Bone, L. W., & Singer, S. (1991). U.S. Pat. No. 5,045,314 de Oliveira, E. J., Rabinovitch, L., Monnerat, R. G., Passos, L. K., & Zahner, V. (2004). Molecular characterization of *Brevibacillus laterosporus* and its potential use in biological control. *Appl Environ Microbiol*, 70(11), 6657-6664.

Favret, M. E. and Yousten, A. A. (1985) Insecticidal activity of *Bacillus laterosporus*. *J. Invertebrate Pathology* 48, 195-203.

Huang, X., Tian, B., Niu, Q., Yang, J., Zhang, L., & Zhang, K. (2005). An extracellular protease from *Brevibacillus laterosporus* G4 without parasporal crystals can serve as a pathogenic factor in infection of nematodes. *Res Microbiol*, 156(5-6), 719-727.

Orlova, M. V., Smirnova, T. A., Ganushkina, L. A., Yacubovich, V. Y., & Azizbekyan, R. R. (1998). Insecticidal activity of *Bacillus laterosporus*. *Appl Environ Microbiol*, 64(7), 2723-2725.

Rivers, D. B., Vann, C. N., Zimmack, H. L., & Dean, D. H. (1991). Mosquitocidal activity of *Bacillus laterosporus*. *Journal of Invertebrate Pathology*, 58, 444-447.

Ruiu, L., Delrio, G., Ellar, D. J., Floris, I., Paglietti, B., Rubino, S., et al. (2006). Lethal and sublethal effects of *Brevibacillus laterosporus* on the housefly (*Musca domestica*). *Entomologia Experimentalis et Applicata*, 118(2), 137-144.

Schnepf, H. E., Narva, K. E., Stockhoff, B. A., Finstad Lee, S., Walz, M., & Sturgis, B. (2002). United States Patent No. US 2002/0120114A1.

Singer, S. (1996). The utility of strains of morphological group II *Bacillus*. *Advances in applied microbiology*, 42, 219-261.

Singer, S., Van Fleet, A. L., Viel, J. J., & Genevese, E. E. (1997). Biological control of the zebra mussel *Dreissena polymorpha* and the snail *Biomphalaria glabrata*, using Gramicidin S and D and molluscicidal strains of *Bacillus*. *Journal of Industrial Microbiology and Biotechnology*, 18(4), 226-231.

Singh, P. (1983) A general purpose laboratory diet mixture for rearing insects. *Insect Sci. Application* 4, 357-362.

Tabashnik, B. E., Cushing, N. L., Finson, N., Johnson, M. W. (1990) Field Development of Resistance to *Bacillus thuringiensis* in Diamondback Moth (Lepidoptera: Plutellidae). *Journal of Economic Entomology*, 83, 1671-1676.

Tabashnik, B. E., Liu, Y., Malvar, T., Heckel, D. G., Masson, L. and Ferré, J. (1998) Insect resistance to *Bacillus thuringiensis*: uniform or diverse? *Phil. Trans. R. Soc. Lond. B* 29 October 353, 1751-1756.

Wearing, C. H. et al., (2003) Screening for resistance in apple cultivars to light brown apple moth, *Epiphyas postvittana* and green headed leaf roller *Planotortrix octo* and its relationship to field damage. *Entomologia Experimentalis et Applicata* 109, 39-53.

Zahner, V., Rabinovitch, L., Suffys, P., & Momen, H. (1999). Genotypic diversity among *Brevibacillus laterosporus* strains. *Applied and environmental microbiology*, 65(11), 5182.

The invention claimed is:

1. A method for controlling at least one pest, the method comprising contacting the at least one pest with a composition comprising at least one strain of *Brevibacillus laterosporus* and an agriculturally acceptable carrier, wherein the strain is selected from *Brevibacillus laterosporus* strain NMI No. V12/001946, *Brevibacillus laterosporus* strain NMI No. V12/001945, and *Brevibacillus laterosporus* strain V12/001944.

2. The method according to claim 1, wherein the at least one pest is an insect.

3. The method according to claim 2, wherein the insect is selected from a *Lepidoptera* species or a *Diptera* species.

4. The method according to claim 3, wherein the at least one insect is from a *Lepidoptera* species.

5. The method according to claim 4, wherein the *Lepidoptera* is selected from the group consisting of *Tortricidae* and Plutellidae.

6. The method according to claim 4, wherein the *Lepidoptera* species is selected from the group consisting of codling moth (*Cydia pomonella*), common forest looper moth (Pseudocoremia suavis), cotton bollworm moth (Helicoverpa armigera), light brown apple moth (Epiphyas postvittana), blacklegged leafroller moth (Planotortrix notophaea), black lyre leafroller moth (Cnephasia jactatana) diamond back moth (*Plutella xylostella*), and cabbage looper moth (*Trichoplusia nl*).

7. The method according to claim 3, wherein the *Diptera* species is a mosquito species.

8. The method according to claim 7, wherein the mosquito species is selected from *Culex* pervigilans and Opifex fuscus.

9. The method according to claim 1, wherein the pest is a nematode.

10. The method according to claim 9, wherein the nematode is a microworm.

11. The method according to claim 10, wherein the microworm is Panagrellus redivivus.

12. The method according to claim 1, wherein the pest is a wasp.

13. The method according to claim 12, wherein the wasp is Vespula *vulgaris*.

* * * * *

SEQUENCE LISTING

```
<160> NUMBER OF SEQ ID NOS: 4

<210> SEQ ID NO 1
<211> LENGTH: 1483
<212> TYPE: DNA
<213> ORGANISM: Brevibacillus laterosporus

<400> SEQUENCE: 1
acgctggcgg cgtgcctaat acatgcaagt cgagcgaggg tcttcggacc ctagcggcgg      60
acgggtgagt aacacgtagg caacctgcct gtaagactgg gataacatag ggaaacttat     120
gctaataccg gataggtttt tgcttctcct gaagcgaaac ggaaagatgg cgcaagctat     180
cacttacaga tgggcctgcg gcgcattagc tagttggtga ggtaatggct caccaaggcg     240
acgatgcgta gccgacctga gagggtgacc ggccacactg ggactgagac acggcccaga     300
ctcctacggg aggcagcagt agggaatttt ccacaatgga cgaaagtctg atggagcaac     360
gccgcgtgaa cgatgaaggc tttcgggtcg taaagttctg ttgttaggga agaaacagtg     420
ccatttaaat aaggtggcac cttgacggta cctaacgaga aagccacggc taactacgtg     480
```

```
ccagcagccg cggtaatacg taggtggcaa gcgttgtccg gaattattgg gcgtaaagcg      540
cgcgcaggtg gctatgtaag tctgatgtta agcccgagg ctcaacctcg gttcgcattg       600
gaaactgtgt agcttgagtg caggagagga aagtggtatt ccacgtgtag cggtgaaatg      660
cgtagagatg tggaggaaca ccagtggcga aggcgacttt ctggcctgta actgacactg      720
aggcgcgaaa gcgtggggag caaacaggat tagataccct ggtagtccac gccgtaaacg      780
atgagtgcta ggtgttaggg gtttcaatac ccttagtgcc gcagctaacg caataagcac      840
tccgcctggg gagtacgctc gcaagagtga aactcaaagg aattgacggg ggcccgcaca      900
agcggtggag catgtggttt aattcgaagc aacgcgaaga accttaccag gtcttgacat      960
cccactgacc gctctagaga tagagcttcc cttcggggca gtggtgacag gtggtgcatg     1020
gttgtcgtca gctcgtgtcg tgagatgttg ggttaagtcc gcaacgagc gcaacccttta     1080 tctttagttg ccagcattca gttgggcact ctagagagac tgccgtcgac aagacggagg     1140
aaggcgggga tgacgtcaaa tcatcatgcc cctatgacc tgggctacac acgtgctaca     1200
atggttggta caacgggatg ctacttcgcg agaagatgct aatctcttaa aaccaatctc     1260
agttcggatt gtaggctgca actcgcctac atgaagtcgg aatcgctagt aatcgcggat     1320
cagcatgccg cggtgaatac gttcccgggc cttgtacaca ccgcccgtca caccacggga     1380
gtttgcaaca cccgaagtcg gtgaggtaac gcaaggagc cagccgccga aggtgggta      1440 gataactggg gtgaagtcgt aacaaggtat ccgtaccgga agg                        1483

<210> SEQ ID NO 2
<211> LENGTH: 1483
<212> TYPE: DNA
<213> ORGANISM: Brevibacillus laterosporus

<400> SEQUENCE: 2
acgctggcgg cgtgcctaat acatgcaagt cgagcgaggg tcttcggacc ctagcggcgg       60
acgggtgagt aacacgtagg caacctgcct gtaagactgg gataacatag ggaaacttat      120
gctaataccg gatagggttt tgcttctcct gaagcgaaac ggaaagatgg cgcaagctat      180
cacttgcaga tgggcctgcg gcgcattagc tagttggtga ggtaatggct caccaaggcg      240
acgatgcgta gccgacctga gagggtgacc ggccacactg ggactgagac acggcccaga      300
ctcctacggg aggcagcagt agggaatttt ccacaatgga cgaaagtctg atggagcaac      360
gccgcgtgaa cgatgaaggc tttcgggtcg taaagttctg ttgttaggga agaaacagtg      420
ccatttaaat aaggtggcac cttgacggta cctaacgaga aagccacggc taactacgtg      480
ccagcagccg cggtaatacg taggtggcaa gcgttgtccg gaattattgg gcgtaaagcg      540
cgcgcaggtg gctatgtaag tctgatgtta agcccgagg ctcaacctcg gttcgcattg       600
gaaactgtgt agcttgagtg caggagagga aagtggtatt ccacgtgtag cggtgaaatg      660
cgtagagatg tggaggaaca ccagtggcga aggcgacttt ctggcctgta actgacactg      720
aggcgcgaaa gcgtggggag caaacaggat tagataccct ggtagtccac gccgtaaacg      780
atgagtgcta ggtgttaggg gtttcaatac ccttagtgcc gcagctaacg caataagcac      840
tccgcctggg gagtacgctc gcaagagtga aactcaaagg aattgacggg ggcccgcaca      900
agcggtggag catgtggttt aattcgaagc aacgcgaaga accttaccag gtcttgacat      960
cccactgacc gctctagaga tagagcttcc cttcggggca gtggtgacag gtggtgcatg     1020
gttgtcgtca gctcgtgtcg tgagatgttg ggttaagtcc gcaacgagc gcaacccttta     1080 tctttagttg ccagcattca gttgggcact ctagagagac tgccgtcgac aagacggagg     1140
```

```
aaggcgggga tgacgtcaaa tcatcatgcc ccttatgacc tgggctacac acgtgctaca    1200
atggttggta caacgggatg ctacttcgcg agaagatgct aatctcttaa aaccaatctc    1260
agttcggatt gtaggctgca actcgcctac atgaagtcgg aatcgctagt aatcgcggat    1320
cagcatgccg cggtgaatac gttcccgggc cttgtacaca ccgcccgtca ccaccgggag    1380
gtttgcaaca cccgaagtcg gtgaggtaac cgcaaggagc cagccgccga aggtggggta    1440
gataactggg gtgaagtcgt aacaaggtat ccgtaccgga agg                     1483

<210> SEQ ID NO 3
<211> LENGTH: 1483
<212> TYPE: DNA
<213> ORGANISM: Brevibacillus laterosporus

<400> SEQUENCE: 3
acgctggcgg cgtgcctaat acatgcaagt cgagcgaggg tcttcggacc ctagcggcgg      60
acgggtgagt aacacgtagg caacctgcct gtaagactgg gataacatag ggaaacttat     120
gctaataccg gataggtttt gcttctcct ggagcgaaac ggaaagatgg cgcaagctat      180
cacttacaga tgggcctgcg gcgcattagc tagttggtga ggtaatggct caccaaggcg     240
acgatgcgta gccgacctga gagggtgacc ggccacactg gactgagac acggcccaga     300 ctcctacggg aggcagcagt agggaatttt ccacaatgga cgaaagtctg atggagcaac     360
gccgcgtgaa cgatgaaggc tttcgggtcg taaagttctg ttgttaggga agaaacagtg     420
ccatttaaat aaggtggcac cttgacggta cctaacgaga aagccacggc taactacgtg     480
ccagcagccg cggtaatacg taggtggcaa gcgttgtccg gaattattgg gcgtaaagcg     540
cgcgcaggtg gctatgtaag tctgatgtta aagcccgagg ctcaacctcg gttcgcattg     600
gaaactgtgt agcttgagtg caggagagga aagtggtatt ccacgtgtag cggtgaaatg     660
cgtagagatg tggaggaaca ccagtggcga aggcgacttt ctggcctgta actgacactg     720
aggcgcgaaa gcgtggggag caaacaggat tagataccct ggtagtccac gccgtaaacg     780
atgagtgcta ggtgttaggg gtttcaatac ccttagtgcc gcagctaacg caataagcac     840
tccgcctggg gagtacgctc gcaagagtga aactcaaagg aattgacggg ggcccgcaca     900
agcggtggag catgtggttt aattcgaagc aacgcgaaga accttaccag gtcttgacat     960
cccactgacc gctctagaga tagagcttcc cttcggggca gtggtgacag gtggtgcatg    1020
gttgtcgtca gctcgtgtcg tgagatgttg ggttaagtcc cgcaacgagc gcaacccta    1080 tctttagttg ccagcattca gttgggcact ctagagagac tgccgtcgac aagacggagg    1140
aaggcgggga tgacgtcaaa tcatcatgcc ccttatgacc tgggctacac acgtgctaca    1200
atggttggta caacgggatg ctacttcgcg agaagatgct aatctcttaa aaccaatctc    1260
agttcggatt gtaggctgca actcgcctac atgaagtcgg aatcgctagt aatcgcggat    1320
cagcatgccg cggtgaatac gttcccgggc cttgtacaca ccgcccgtca ccaccgggag    1380
gtttgcaaca cccgaagtcg gtgaggtaac cgcaaggagc cagccgccga aggtggggta    1440
gataactggg gtgaagtcgt aacaaggtat ccgtaccgga agg                     1483

<210> SEQ ID NO 4
<211> LENGTH: 1483
<212> TYPE: DNA
<213> ORGANISM: Brevibacillus laterosporus

<400> SEQUENCE: 4
```

-continued

```
acgctggcgg cgtgcctaat acatgcaagt cgagcgaggg ttttcggacc ctagcggcgg     60
acgggtgagt aacacgtagg caacctgcct gtaagactgg gataacatag ggaaacttat    120
gctaataccg gatagagttt tgcttcgcat gaagcgaaac ggaaagatgg cgcaagctat    180
cacttgcaga tgggcctgcg gcgcattagc tagttggtga ggtaaaggct caccaaggcg    240
acgatgcgta gccgacctga gagggtgacc ggccacactg ggactgagac acggcccaga    300
ctcctacggg aggcagcagt agggaatttt ccacaatgga cgaaagtctg atggagcaac    360
gccgcgtgaa cgatgaaggc tttcgggtcg taaagttctg ttgttaggga agaaacagtg    420
ccatttaaat aaggtggcac cttgacggta cctaacgaga aagccacggc taactacgtg    480
ccagcagccg cggtaatacg taggtggcaa gcgttgtccg gaattattgg gcgtaaagcg    540
cgcgcaggtg gctatgtaag tctgatgtta aagcccgggg ctcaacctcg gttcgcattg    600
gaaactgcgt agcttgagtg caggagagga aagtggtatt ccacgtgtag cggtgaaatg    660
cgtagagatg tggaggaaca ccagtggcga aggcgacttt ctggcctgta actgacactg    720
aggcgcgaaa gcgtggggag caaacaggat tagataccct ggtagtccac gccgtaaacg    780
atgagtgcta ggtgttaggg gtttcaatac ccttagtgcc gcagctaacg caataagcac    840
tccgcctggg gagtacgctc gcaagagtga aactcaaagg aattgacggg ggcccgcaca    900
agcggtggag catgtggttt aattcgaagc aacgcgaaga accttaccag gtcttgacat    960
cccactgacc gctctagaga tagagcttcc cttcggggca gtggtgacag gtggtgcatg   1020
gttgtcgtca gctcgtgtcg tgagatgttg ggttaagtcc cgcaacgagc gcaaccctta   1080
tctttagttg ccagcattca gttgggcact ctagagagac tgccgtcgac aagacggagg   1140
aaggcgggga tgacgtcaaa tcatcatgcc ccttatgacc tgggctacac acgtgctaca   1200
atggttggta caacgggatg ctacttcgcg agaagatgct aatctcttaa aaccaatctc   1260
agttcggatt gtaggctgca actcgcctac atgaagtcgg aatcgctagt aatcgcggat   1320
cagcatgccg cggtgaatac gttcccgggc cttgtacaca ccgcccgtca caccacggga   1380
gtttgcaaca cccgaagtcg gtgaggtaac cgcaaggagc cagccgccga aggtggggta   1440
gataactggg gtgaagtcgt aacaaggtat ccgtaccgga agg                      1483
```